(12) United States Patent
Wang et al.

(10) Patent No.: US 10,913,797 B2
(45) Date of Patent: Feb. 9, 2021

(54) ANTI-PD-1 ANTIBODIES AND THERAPEUTIC USES THEREOF

(71) Applicant: Lyvgen Biopharma Holdings Limited, Grand Cayman (KY)

(72) Inventors: Jieyi Wang, Belmont, CA (US); Liqun Dong, San Diego, CA (US); Yaolin Wang, Short Hills, NJ (US)

(73) Assignee: Lyvgen Biopharma Holdings Limited, Grand Cayman (KY)

( * ) Notice: Subject to any disclaimer, the term of this patent is extended or adjusted under 35 U.S.C. 154(b) by 295 days.

(21) Appl. No.: 15/777,015

(22) PCT Filed: Nov. 17, 2016

(86) PCT No.: PCT/US2016/062407
§ 371 (c)(1),
(2) Date: May 17, 2018

(87) PCT Pub. No.: WO2017/087599
PCT Pub. Date: May 26, 2017

(65) Prior Publication Data
US 2018/0346569 A1    Dec. 6, 2018

(30) Foreign Application Priority Data
Nov. 18, 2015 (CN) .......................... 2015 1 0799538

(51) Int. Cl.
*C07K 16/28* (2006.01)
*A61P 35/00* (2006.01)
*C07K 16/22* (2006.01)
*C12N 15/62* (2006.01)
*A61K 39/00* (2006.01)

(52) U.S. Cl.
CPC .......... *C07K 16/2818* (2013.01); *A61P 35/00* (2018.01); *C07K 16/22* (2013.01); *C12N 15/62* (2013.01); *A61K 2039/505* (2013.01); *C07K 2317/24* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2004/0197328 A1* 10/2004 Young ................ A61K 51/1096
424/141.1
2013/0291136 A1   10/2013 Freeman et al.
2015/0165025 A1   7/2015  Korman et al.
2015/0203579 A1   7/2015  Papadopoulos et al.
2015/0232555 A1   8/2015  Carven et al.
2016/0272708 A1   9/2016  Chen

FOREIGN PATENT DOCUMENTS

| WO | 2006/121168 A1 | 11/2006 |
|---|---|---|
| WO | 2008/156712 A1 | 12/2008 |
| WO | 2010/036959 A2 | 4/2010 |
| WO | 2012/145493 A1 | 10/2012 |
| WO | 2013/169693    | 11/2013 |
| WO | 2013/169693 A1 | 11/2013 |
| WO | 2014/206107 A1 | 12/2014 |
| WO | 2015/035606 A1 | 3/2015 |
| WO | 2015/075725 A1 | 5/2015 |
| WO | 2015/112800 A1 | 7/2015 |

OTHER PUBLICATIONS

Chames et al (British J. of Pharmacology, 2009, 157, 220-233) (Year: 2009).*
Kaiser (Science, 2006, 313: 1370) (Year: 2006).*
Gura (Science, 1997, 278:1041-1042) (Year: 1997).*
Almagro & Fransson, Frontiers in Bioscience 2008; 13:1619-33 (Year: 2008).*
Mahoney, K. M., et al., "The Next Immune-Checkpoint Inhibitors: PD-1/PD-L1 Blockade in Melanoma," Clinical Therapeutics., vol. 37, No. 4 Apr. 1, 2015.
PCT/US2016/062407, Feb. 7, 2017, International Search Report and Written Opinion.
PCT/US2016/062407, May 31, 2018, International Preliminary Report on Patentability.
Mahoney, K. M., et al., "The Next Immune-Checkpoint Inhibitors: PD-1/PD-L1 Blockade in Melanoma," Clinical Therapeutics., vol. 37, No. 4 , pp. 764-782 (Apr. 1, 2015).
Selby, Mark J. et al. "Preclinical Development of Ipilimumab and Nivolumab Combination Immunotherapy:Mouse Tumor Models, In Vitro FunctionalStudies, and Cynomolgus Macaque Toxicology," PLOS ONE | DOI:10.1371/journal.pone.0161779 Sep. 9, 2016, pp. 1-19.
Bekerman, Elena et al. "PD-1 Blockade and TLR7 Activation Lack Therapeutic Benefitin Chronic Simian Immunodeficiency Virus-Infected Macaqueson Antiretroviral Therapy," Antimicrobial Agents and Chemotherapy, Nov. 2019 vol. 63 Issue 11 e01163-19, pp. 1-13.

* cited by examiner

*Primary Examiner* — Peter J Reddig
(74) *Attorney, Agent, or Firm* — McDermott Will & Emery LLP

(57) ABSTRACT

Anti-PD-1 antibodies and uses thereof in treating diseases associated with the PD-1 signaling, such as cancer, infectious diseases such as viral infection or immune related diseases.

23 Claims, 15 Drawing Sheets
Specification includes a Sequence Listing.

```
Chothia          1234567890123456789012345678901234567890123456789012345678 90
                          10        20        30        40        50        60
Ordinal          123456789012345678901234567890123456789012345678901234567890
                          10        20        30        40        50        60
SHB-617_VL       NIQMTQSPSSLLSASVGDRVTLSCKAGQNVNNYLAWYQQKLGEPPKVLIFWANSLQTGVPS
VK1-L1           DIQMTQSPSSLSASVGDRVTITCRASQGISNYLAWFQQKPGKAPKSLIYAASSLQSGVPS
JK4                                                                         
                                       L1                         L2

Chothia          123456789012345678901234567890123456789012345678 90123456 78
                          70        80        90       100
Ordinal          1234567890123456789012345678901234567890123456 78
                          70        80        90       100
SHB-617_VL       RFSGSGSGTDFTLTISSLQPEDVATYFCQQYNSWTTFGAGTKLELKR
VK1-L1           RFSGSGSGTDFTLTISSLQPEDFATYYCQQYNSYP
JK4                                                  LTFGGGTKVEIK-
                                             L3
```

Fig. 2

```
Chothia              10         20           30          40         50
Ordinal     123456789012345678901234567890abc234567890123456789012345678
SHB-617_VH  QVTLKESGPGILQPSQTLSLTCSFSGFSLSTSGTCVSWIRQPSGKGLEWLATICWEDSKG
VH2-2-70    QVTLKESGPALVKPTQTLTLTCTFSGFSLSTSGMRVSWIRQPPGKALEWLARIDWDDDKP
JH4         -----------------------------------------------------------
                                    H1                              H2

Chothia      60         70         80         90        100        110         120
Ordinal     9012345678901234567890123456789012abc3456789012345678901234567890123456789012
SHB-617_VH  YNPSLKNRLTISKDTSNNQAFLKITSVDTADSAIYYCARPEDSGYFWPPYW-----YPDYWGQGTLVSVS
VH2-2-70    YSTSLKTRLTISKDTSKNQVVLTMTNMDPVDTATYYCARI---------------------------
JH4         ---------------------------------------------------YPDYWGQGTLVTVS
                                                       H3

Chothia     3
Ordinal     1
SHB-617_VH  S
VH2-2-70    -
JH4         S
```

Fig. 3

Fig. 14
A.
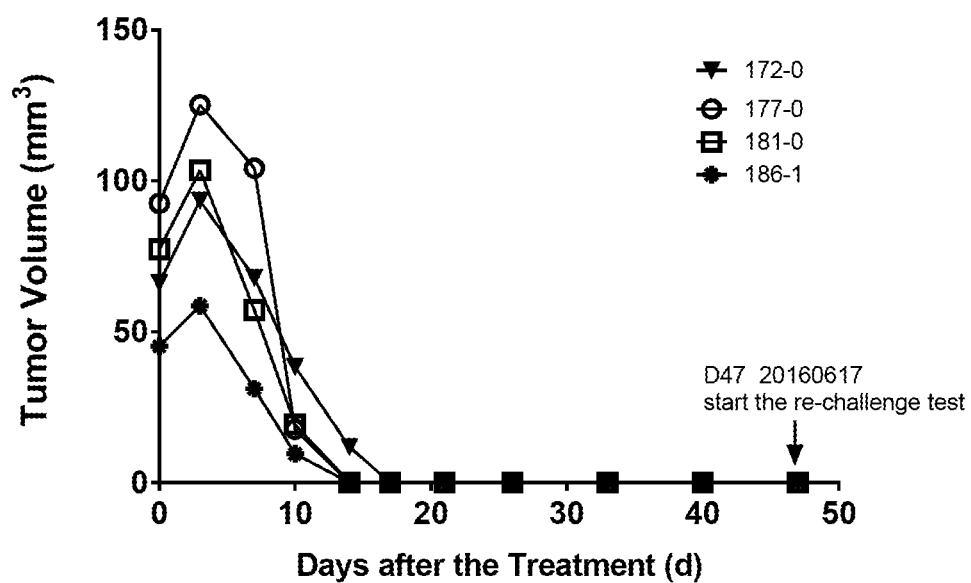
B.
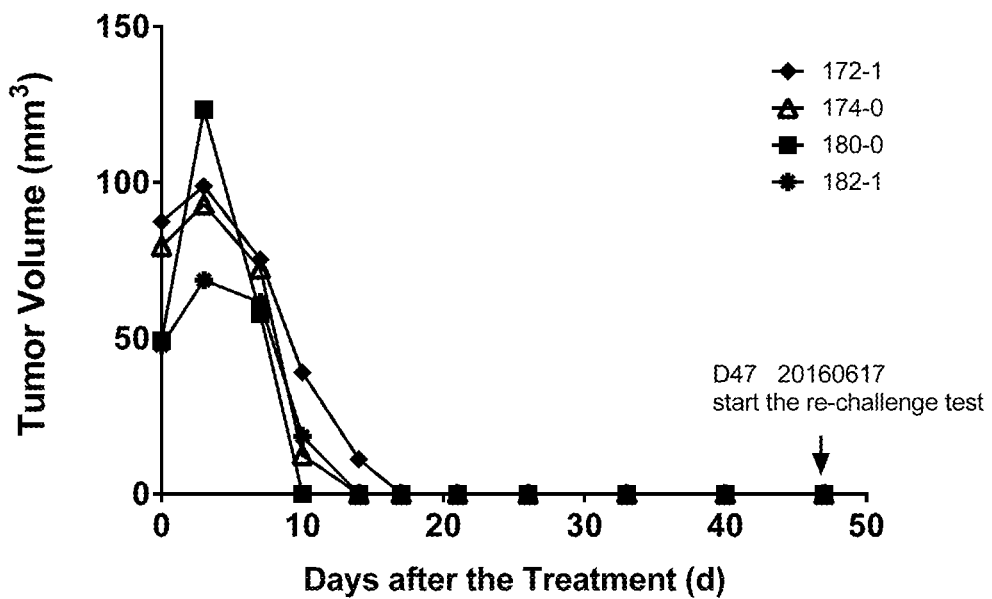

A.

Fig. 16 (Cont'd)
B.
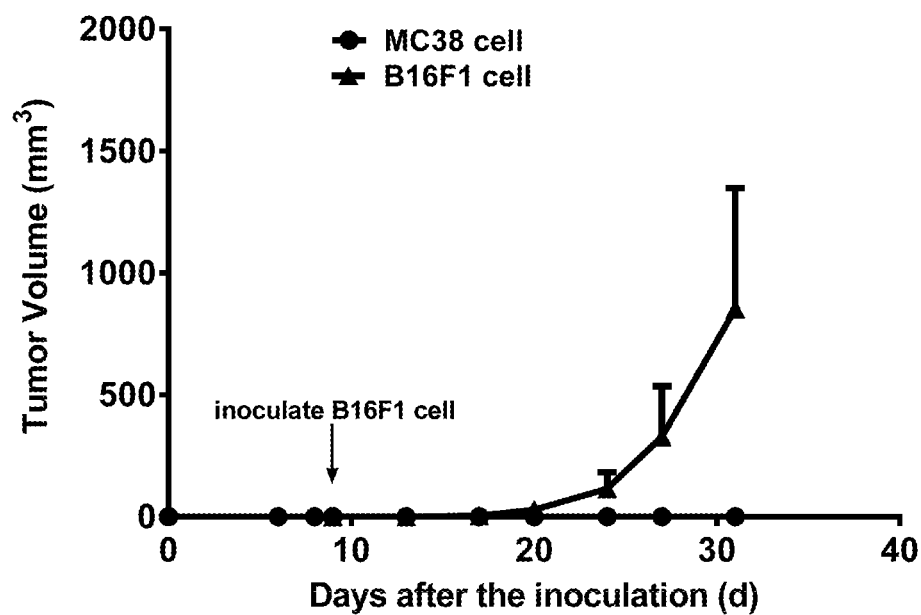
C.
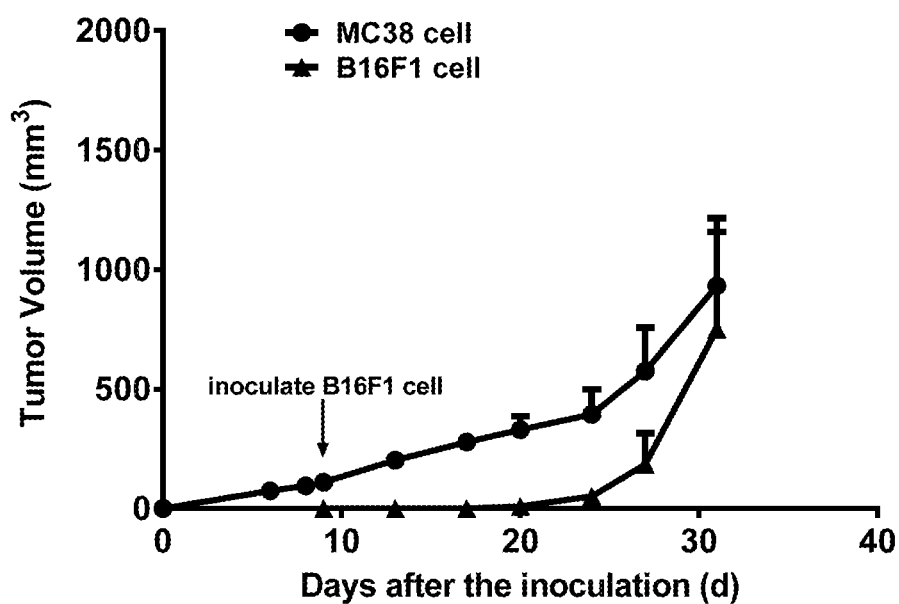

ANTI-PD-1 ANTIBODIES AND THERAPEUTIC USES THEREOF

CROSS-REFERENCE TO RELATED APPLICATION

This application is a national stage filing under 35 U.S.C. 371 of International patent application Ser. No. PCT/US2016/062407, filed Nov. 17, 2016, entitled "ANTI-PD-1 ANTIBODIES AND THERAPEUTIC USES THEREOF," which claims the benefit of the filing date of Chinese Patent Application No. 2015107995388, entitled "Anti-PD-1 Antibodies and Therapeutic Uses Thereof," filed Nov. 18, 2015, the contents of each of which are herein incorporated by reference in its entirety.

SEQUENCE LISTING

This application contains a Sequence Listing in computer readable form (filename: L083970000US00-SEQ-YJC.txt, 26.4 KB (27,060 bytes)—ASCII text file; created May 16, 2018), which is incorporated by reference herein in its entirety and forms part of the disclosure.

BACKGROUND OF THE INVENTION

Programmed cell death protein 1 (PD-1), also known as CD279, is a cell surface receptor expressed on immune cells including T cells. PD-1 binds two ligands, PD-L1 and PD-L2. Binding of PD-1 to its ligand triggers the PD-1-mediated signaling pathway, which is believed to negatively regulate immune responses. PD-1 is an Immunoglobulin (Ig) superfamily member which includes CD28, and CTLA-4. PD-1 and other family members are type I transmembrane glycoproteins containing extracellular Ig domains responsible for ligand binding and a cytoplasmic tail that binds signaling mediator molecules (Keir M E et al. Annu Rev Immunol. 2008; 26:677-704). The cytoplasmic tail of PD-1 contains two tyrosine-based signaling motifs, an ITIM (immunoreceptor tyrosine-based inhibition motif) and an ITSM (immunoreceptor tyrosine-based switch motif). Following stimulation, PD-1 recruits the tyrosine phosphatase SHP-2 to the ITSM motif, leading to the dephosphorylation of T cell effector molecules such as CD3 zeta, PKC theta and ZAP70.

PD-1 knockout mice developed spontaneous autoimmune diseases including lupus-like proliferative arthritis (Nishimura H. et al., 1998, Int. Immunol. 10: 1563-1572), fatal cardiomyopathy (Nishimura H. et al., 2001, Science 291: 319-322) and type I diabetes (Wang J. et al., Proc. Natl. Acad. Sci. U.S.A., 2005, 102: 11823-11828). Overall, analysis of the knockout animals has led to the understanding that PD-1 functions mainly in inducing and regulating peripheral tolerance. Thus, therapeutic blockade of the PD-1 pathway may be helpful in overcoming immune tolerance. Such selective blockade may be of use in the treatment of cancer or infection as well as in boosting immunity during vaccination (either prophylactic or therapeutic).

Tumors evade immune surveillance by creating an immune suppressive microenvironment. Expression of PD-1 and PD-L1 on tumor infiltrating lymphocytes or tumor cells has been found in a number of primary tumor biopsies and is known to contribute to the immune evasion (Ribas A. Cancer Discov. 2015, 5(9):915-9). Such tissues include cancers of the lung, liver, ovary, cervix, skin, colon, glioma, bladder, breast, kidney, esophagus, stomach, oral squamous cell, urothelial cell, and pancreas as well as tumors of the head and neck (Brown et al., J. Immunol., 2003, 170:1257-1266; Dong et al., Nat. Med., 2003, 8:793-800; Wintterle et al., Cancer Res., 2003, 63: 7462-7467; Strome et al., Cancer Res., 2003, 63: 6501-6505; Thompson et al., Cancer Res., 2006, 66: 3381-5; Thompson et al., Clin. Cancer Res., 2007, 13: 1757-61; Nomi T. et al., Clin. Cancer Res., 2007, 13: 2151-7).

PD-1, functioning as an immune checkpoint, plays an important role in down regulating the immune system by preventing the activation of T-cells, which in turn reduces autoimmunity and promotes self-tolerance. The inhibitory effect of PD-1 is accomplished through a dual mechanism of promoting apoptosis in antigen specific T-cells in lymph nodes while simultaneously reducing apoptosis in regulatory T cells. Given its immune suppressive role, PD-1 inhibitors are believed to activate the immune system to attack tumors and are therefore used to treat cancer and other immune related diseases. Blockade of the interactions between PD-1 and its ligands enhances tumor-specific CD8 T-cell immunity that is capable of eliminating tumor cells (Topalian S. et al. Curr Opin Immunol. 2012, 24(2):207-12). Indeed, antibodies against PD-1 or its ligand PD-L1 have shown clinical utilities in the treatment of melanoma and lung cancer.

SUMMARY OF THE INVENTION

The present disclosure is based on the development of an anti-PD-1 antibody, SSI-361, which showed high binding affinity to PD-1 and successfully blocked PD-1-mediated signaling and enhanced T cell activation.

Accordingly, one aspect of the present disclosure provides an isolated anti-PD-1 antibody, which may comprise the same heavy chain variable region complementary determining regions (CDRs) and/or the same light chain variable region CDRs as antibody SSI-361. Such an antibody may comprising: (i) a heavy chain variable region ($V_H$) that comprises a heavy chain complementary determining region (HC CDR) 1 set forth as GFSLSTSGT (SEQ ID NO:13), a HC CDR2 set forth as CWEDS (SEQ ID NO:14), and a HC CDR3 set forth as EDSGYFWFPY (SEQ ID NO:15); and (ii) a light chain variable region ($V_L$) that comprises a light chain complementary determining region (LC CDR) 1 set forth as KAGQNVNNYLA (SEQ ID NO:16), a LC CDR2 set forth as NANSLQT (SEQ ID NO:17); and a LC CDR3 set forth as QQYNSWTT (SEQ ID NO:18).

In some embodiments, the isolated anti-PD-1 antibody described herein comprises a $V_H$ chain that comprises an amino acid sequence at least 80% (e.g., 85%, 90%, 95%, 97%, or above) identical to QVTLKESGPALVKPTQTLTLTCTFSGFSLST-SGTCVSWIRQPPGKALEWLATICWEDS KGY-NPSLKSRLTISKDTSKNQAVLTMTNMDPVDTATYY CARREDSGYFWFPYWGQ GTLVTVSS (SEQ ID NO:12). Alternatively or in addition, the anti-PD-1 antibody comprises a $V_L$ chain that comprises an amino acid sequence at least 80% (e.g., 85%, 90%, 95%, 97%, or above) identical to NIQMTQSPSSLSASVGDRVTITCKAGQNVN-NYLAWYQQKPGKAPKVLIFNANSLQT GVPSRFSGSGSGTDFTLTISSLQPEDFATYYCQQYN-SWTTFGGGTKVEIKR (SEQ ID NO:11).

In some examples, the isolated anti-PD-1 antibody described herein comprises a $V_H$ chain that comprises the amino acid sequence of QVTL-KESGPALVKPTQTLTLTCTFSGFS LST-SGTCVSWIRQPPGKALEWLATICWEDSKGY-NPSLKSRLTISKDTSKNQAVLT MTNMDPVDTATYYCARRED- SGYFWFPYWGQGTLVTVSS (SEQ ID NO:12); and a $V_L$ chain that comprises the amino acid sequence of NIQMTQSPSSLSASVGDRVTITCKAGQNVN- NYLAWYQQKPGKAPKVLIFNANSLQ TGVPSRFSGSGSGTDFTLTISSLQPEDFATYYCQQYN- SWTTFGGGTKVEIKR (SEQ ID NO:11).

In some examples, the anti-PD-1 antibody described herein comprises a $V_H$ chain that comprises the amino acid sequence of QVTLKESGPGILQP- SQTLSLTCSFSGFSLSTSGTCVSWIRQPSGKGLEWLA- TICWED SKGY- NPSLKNRLTISKDTSNNQAFLKITSVDTADSAIYY CARREDSGYFWFPYWG QGTLVSVS (SEQ ID NO:12); and a $V_L$ chain that comprises the amino acid sequence of NIQMTQSPSLLSASVGDRVTLSCKAGQNVN- NYLAWYQQKLGEPPKVLIFNANSLQ TGVPSRFSGSGSGTDFTLTISSLQPEDVATYFCQQYN- SWTTFGAGTKLELKR (SEQ ID NO:11).

In some embodiments, the anti-PD-1 antibody described herein may bind to the same epitope as SSI-361 or competes against SSI-361 for binding to PD-1.

Any of the anti-PD-1 antibodies described herein may be a full-length antibody (e.g., an IgG molecule) or an antigen-binding fragment thereof (e.g., Fab or F(ab')2 or scFv). In some examples, the antibody may be a chimeric antibody or a humanized antibody. In other examples, the antibody described herein may be part of a multi-specific antibody, which binds PD-1 and one or more other target antigens. In yet other examples, the antibody described herein is conjugated with a suitable agent, such as a therapeutic agent or a diagnostic agent, to form a conjugate, e.g., an antibody drug conjugate (ADC).

In another aspect, the present disclosure provides an isolated nucleic acid or a set of nucleic acids, which collectively encodes any of the anti-PD-1 antibodies described herein. Such a nucleic acid may be a vector, such as an expression vector in which a nucleotide sequence encoding one or both of the $V_H$ and $V_L$ chains of the antibody is in operable linkage to a suitable promoter.

In some examples, the isolated nucleic acid encoding the anti-PD-1 antibody comprise a first nucleotide sequence that encodes the $V_H$ and a second nucleotide sequence that encodes the $V_L$. In other examples, the coding sequences of the $V_H$ and $V_L$ chains are located on different nucleic acids.

In yet another aspect, the present disclosure provides a vector or vector set (e.g., containing two vectors), which collectively comprises nucleic acid(s) encoding any of the anti-PD-1 antibodies described herein. Such a host cell can be cultured under suitable conditions allowing for the expression of the antibody. The host cell can then be collected for isolation of the antibody thus produced.

Further, the present disclosure provides a pharmaceutical composition, comprising any of the anti-PD-1 antibodies as described herein (e.g., in free form or conjugated with a suitable agent as described herein) or any of the nucleic acid/nucleic acid set as described herein, and a pharmaceutically acceptable carrier. Such a pharmaceutical composition can be used for treating a disease associated with the PD-1 signaling (e.g., cancer, infectious diseases such as viral infection (e.g., hepatitis A, hepatitis B, or hepatitis C); as well as other immune related diseases.

In another aspect, the present disclosure provides a method for treating a disease associated with PD-1 signaling (e.g., those disclosed herein), the method comprising administering to a subject in need thereof an effective amount of any of the pharmaceutical compositions as described herein, either alone or in combination with one or more other therapeutic agents (e.g., those described herein).

Also within the scope of the present disclosure is the use of any of the anti-PD-1 antibodies, the encoding nucleic acid(s), the antibody conjugates, e.g., ADCs, or a pharmaceutical composition comprising such in manufacturing a medicament for use in treating any of the target diseases described herein.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

FIG. 2 is a comparison of the SHB-617 $V_L$ (SEQ ID NO: 1) domain with Chothia CDR definitions (boxed) and numbering and alignment to the human Acceptor framework. VK1-L1 is SEQ ID NO: 2 and JH4 is SEQ ID NO: 3.

FIG. 3 is a comparison of the SHB-617 $V_H$ (SEQ ID NO: 4) domain with Chothia CDR definitions (boxed) and numbering and alignment to the human Acceptor framework. VH2-2-70 is SEQ ID NO: 5 is and JH4 SEQ ID NO: 6.

Figure 13:
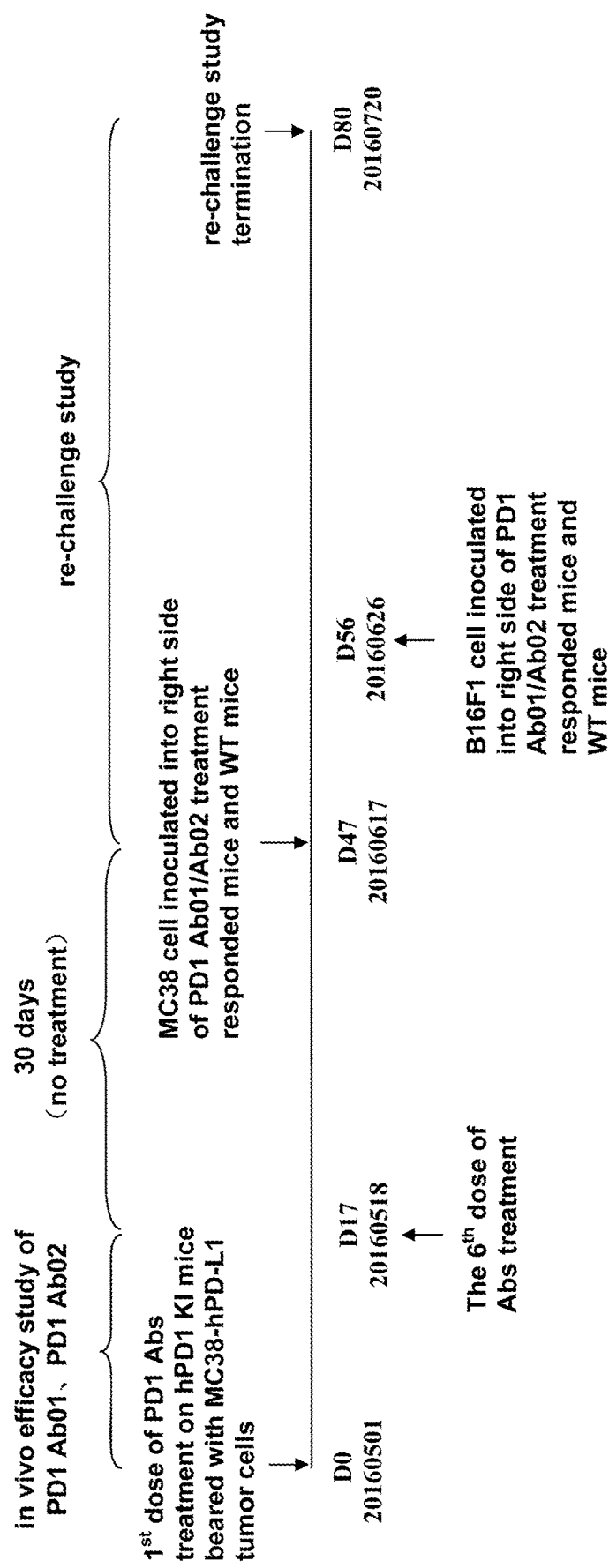

FIG. 13 is a diagram showing an exemplary experimental design for evaluating in vivo tumor treatment efficacy of exemplary anti-PD-1 antibodies.

FIG. 14 includes chart showing the effects of various anti-PD-1 antibodies in suppressing the growth of tumors induced by MC38 cancer cells in hPD-1 KI mice. Panel A: mice treated with PD-1 Ab01 (SSI-361); Panel B: mice treated with PD-1 Ab02 (nivolumab).

Figure 15:
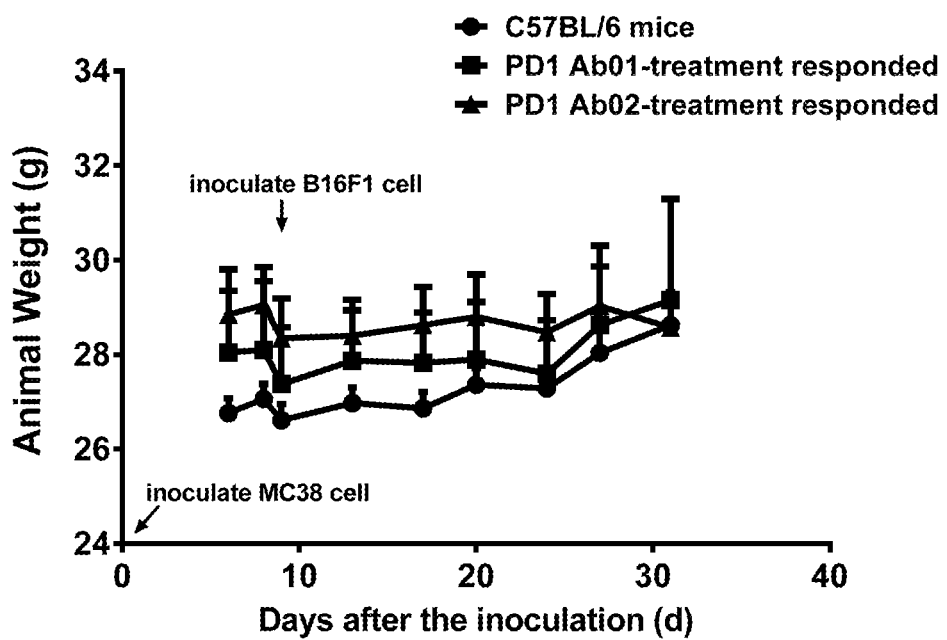

FIG. 15 is a chart showing mice body weight change during the course of anti-PD-1 antibody treatment. B16F1 cell was inoculated into the left side when mean tumor volume of MC38 in C57BL/6 mice reached 110.4 mm$^3$. Error bars represented Mean±SEM. No significant influences on body weight were observed in three study arms.

Figure 16:
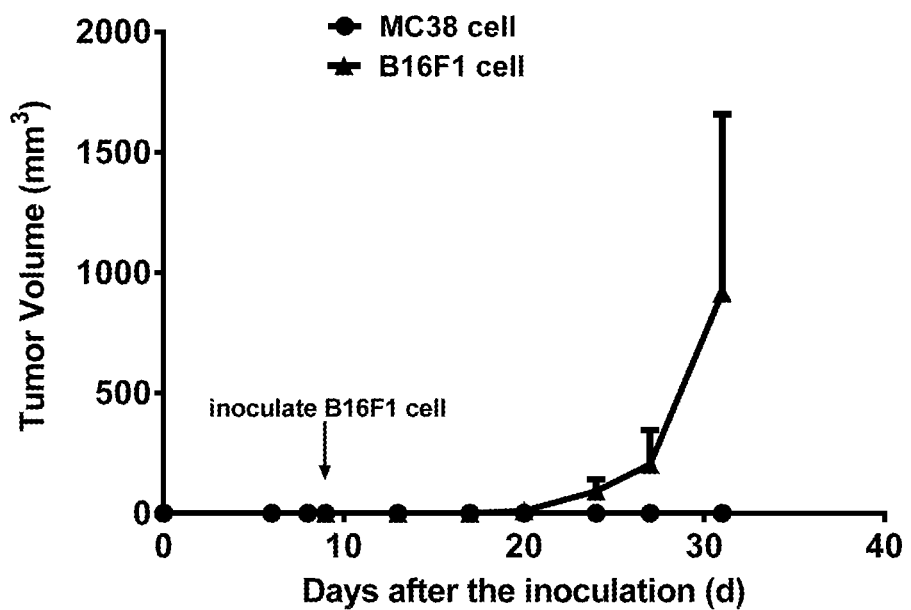

FIG. 16 includes charts showing the anti-tumor effects of the anti-PD-1 antibodies on PD-L1 positive tumors. Each mouse was inoculated subcutaneously into right side with MC38 cancer cell (PD-L1 positive) for tumor development. Tumor volume of all animals was measured twice weekly. When the mean volume of tumors induced by MC38 cells in the C57BL/6 mice reached 110.4 mm$^3$, the animals were then inoculated subcutaneously into the left side with B16F1 cell. Error bars represented Mean±SEM. For MC38 tumors, there was no measurable growth in PD-1 Ab01 and PD-1 Ab02-treated mice (Panels A and B), while in C57BL/6 mice, MC38 tumors showed normal growth curves (Panel C). The growth of B16F1 had no obvious differences in three study arms.

BRIEF DESCRIPTION OF THE SEQUENCES

SEQ ID NO:1 is the amino acid sequence of the $V_L$ chain variable region of SHB-617 $V_L$ associated with FIG. 2.

SEQ ID NO:2 is the amino acid sequence of VK1-L1 associated with FIG. 2.

SEQ ID NO:3 is the amino acid sequence of JK4 associated with FIG. 2.

SEQ ID NO:4 is the amino acid sequence of the $V_H$ chain variable region of SHB-617_VH associated with FIG. 3.

SEQ ID NO:5 is the amino acid sequence of VH2-2-70 associated with FIG. 3.

SEQ ID NO:6 is the amino acid sequence of JH4 associated with FIG. 3.

Figure 4:
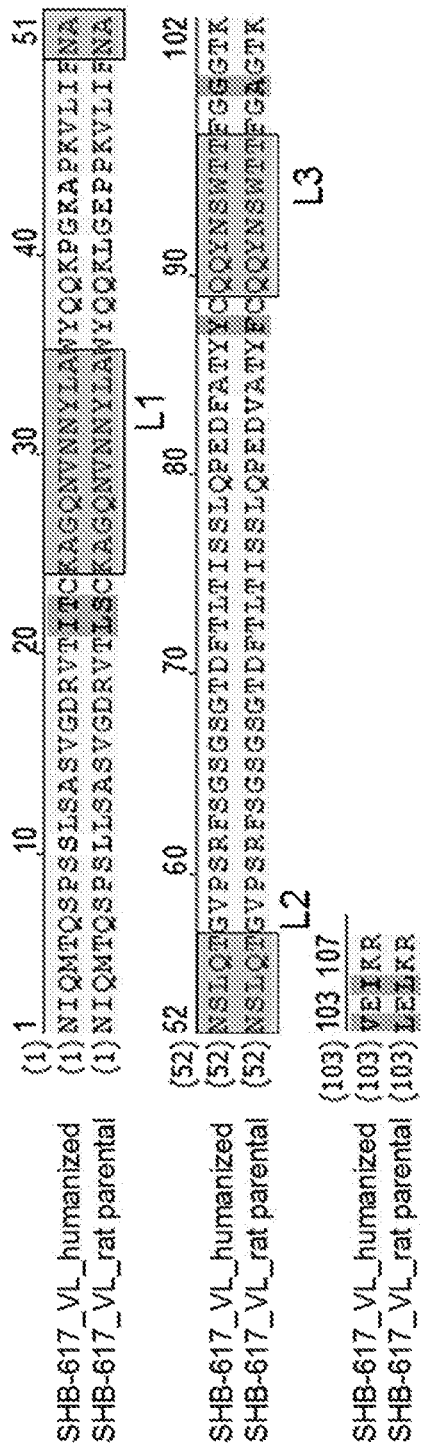
FIG. 4. is an alignment of SHB-617 $V_L$ humanized (SEQ ID NO: 7) and parental rat domains (SEQ ID NO: 8). Boxed are CDR L1, L2 and L3.

SEQ ID NO:7 is the amino acid sequence of humanized SHB-617 (SSI-361) VL as shown in FIG. 4.

SEQ ID NO:8 is the amino acid sequence of parental rat SHB-617 VL as shown in FIG. 4.

Figure 5:
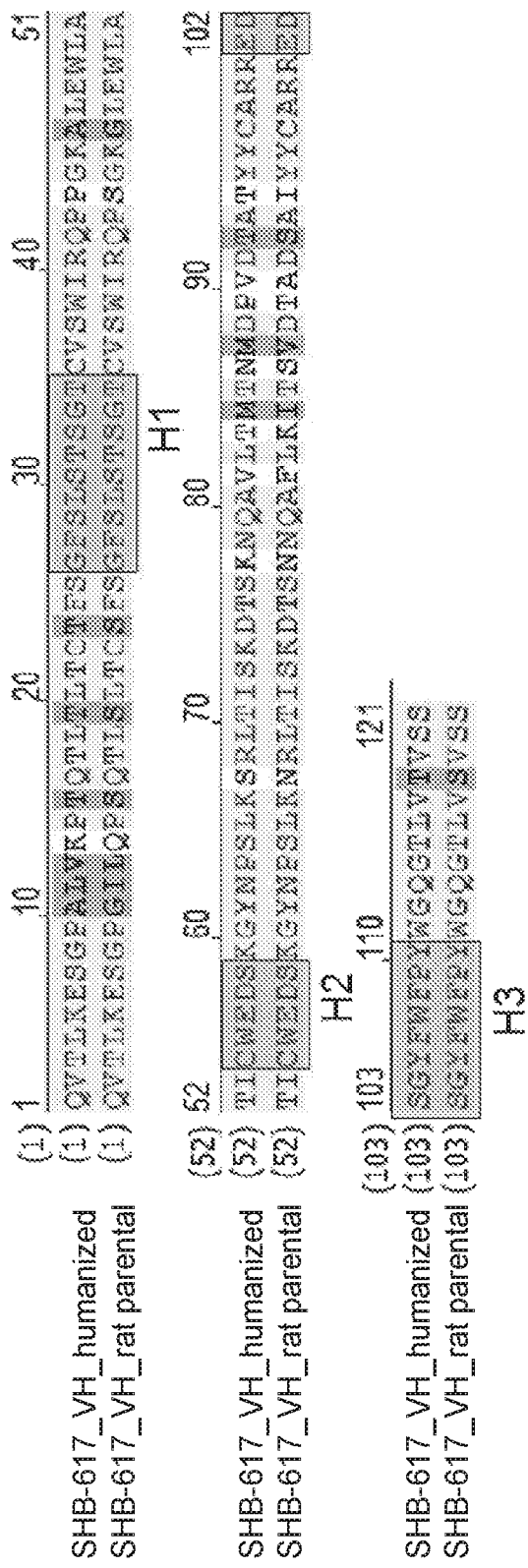
FIG. 5 is an alignment of SHB-617 $V_H$ humanized (SEQ ID NO: 9) and parental rat (SEQ ID NO: 10) domains. Boxed are CDR H1, H2 and H3

SEQ ID NO:9 is the amino acid sequence of humanized SHB-617 (SSI-361) VH as shown in FIG. 5.

SEQ ID NO:10 is the amino acid sequence of parental rat SHB-617 VH as shown in FIG. 5.

SEQ ID NO:11 is the amino acid sequence of SSI-361 (humanized SHB-617) LC SEQ ID NO:12 is the amino acid sequence of SSI-361 (humanized SHB-617) HC.

SEQ ID NOs13-15 refer the amino acid sequence of heavy chain CDR1, heavy chain CDR2, and heavy chain CDR3 of SSI-361, respectively.

SEQ ID NOs:16-18 refer to the amino acid sequence of light chain CDR1, light chain CDR2, and light chain CDR3 of SSI-361, respectively.

SEQ ID NO:19 is the amino acid sequence of the whole heavy chain of SHB-617.

SEQ ID NO:20 is the coding sequence for the whole heavy chain of SHB-617.

SEQ ID NO:21 is the amino acid sequence of the whole light chain of SHB-617

SEQ ID NO:22 is the coding sequence for the whole light chain of SHB-617.

SEQ ID NO:23 is the amino acid sequence of the whole heavy chain of SSI-361.

SEQ ID NO:24 is the amino acid sequence of the whole light chain of SSI-361.

DETAILED DESCRIPTION OF THE INVENTION

Described herein are anti-PD-1 antibodies, nucleic acids encoding such, and uses thereof in enhancing immune responses by activating T cells and treating diseases associated with the PD-1 signaling such as cancer.

Anti-PD-1 Antibodies

PD-1 is a cell surface receptor expressed on immune cells, including T cells and B cells, that negatively regulates immune responses. Human PD-1 is encoded by the PDCD1 gene. As an example, the amino acid sequence of a human PD-1 is disclosed under GenBank accession number NP 005009.

An anti-PD-1 antibody (interchangeably used in plural form) is an immunoglobulin molecule capable of specific binding to a PD-1 protein or a fragment thereof, through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In some examples, the antibody disclosed herein specifically binds a target PD-1 antigen. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to a PD-1 epitope is an antibody that binds this PD-1 epitope with greater affinity, avidity, more readily, and/or with greater duration than it binds to other PD-1 epitopes or non-PD-1 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

An anti-PD-1 antibody is an antibody capable of binding to a PD-1 antigen and inhibits the PD-1-mediated signaling pathway, thereby enhancing immune responses such as T cell activation. In some examples, an anti-PD-1 antibody described herein suppresses the PD-1 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold.

The binding affinity of an anti-PD-1 antibody to the PD-1 antigen can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to PD-1 is by measuring binding affinity of monofunctional Fab fragments of the antibody. To obtain monofunctional Fab fragments, an antibody (for example, IgG) can be cleaved with papain or expressed recombinantly. The affinity of an anti-PD-1 Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

The anti-PD-1 antibody described herein may bind to the same epitope as SHB-617, the amino acid sequences of the $V_H$ and $V_L$ chains of which are provided in FIG. 2 and FIG. 3. Alternatively, the antibody may compete against SHB-617 from binding to the PD-1 target antigen. Such antibodies may exhibit at least 20% (e.g., 30%, 40%, 50%, 60%, 70%, 80%, 90%, or greater) of the activity of inhibiting a signaling pathway mediated by the PD-1 target antigen as relative to SHB-617.

Such an anti-PD-1 antibody may comprise the same heavy chain CDRs and/or the same light chain CDRs as those of SHB-617, for example, the CDR regions highlighted in FIG. 2 and FIG. 3, which are determined by the Chothia numbering scheme. Alternatively or in addition, the anti-PD-1 antibody described herein may comprise a $V_H$ CDR1, $V_H$ CDR2, and $V_H$ CDR3 at least 75% (e.g., 80%, 85%, 90%, 95%, or 98%) identical to the corresponding $V_H$ CDRs of SHB-617, and/or a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of SHB-617.

"Complementarity determining regions" or "CDRs" are known in the art as referring to non-contiguous sequences of amino acids within antibody variable regions, which confer antigen specificity and binding affinity. In general, there are three (3) CDRs in each heavy chain variable region and three (3) CDRs in each light chain variable region. The precise amino acid sequence boundaries of a given CDR can be readily determined using any of a number of well-known schemes, including those described by Kabat et al. (1991), 5th Ed. Public Health Service, National Institutes of Health, Bethesda, Md. (the Kabat" numbering scheme), Al-Lazikani et al., (1997) JMB 273,927-948 (the Chothia" numbering scheme), MacCallum et al., J. Mol. Biol. 262:732-745 (1996) (the Contact numbering scheme), Lefranc M P et al., Dev Comp Immunol, 2003 January; 27(1):55-77 (the IMGT numbering scheme), and Honegger A and Pluckthun A, J Mol Biol, 2001 Jun. 8; 309(3):657-70, (the AHo numbering scheme).

The boundaries of a given CDR may vary depending on the scheme used for identification. For example, the Kabat scheme is based structural alignments, while the Chothia scheme is based on structural information. The Contact scheme is based on analysis of complex crystal structures and is similar in many respects to the Chothia numbering scheme. Thus, unless otherwise specified, the term "complementary determining region" or "CDR" of a given antibody should be understood to encompass the complementary determining region as defined by any of the known schemes described herein above.

If, determined by the same numbering scheme, an antibody has the same $V_H$ and/or $V_L$ CDRs as SHB-617, such an antibody is deemed as having the same CDRs as SHB-617 and is within the scope of the present disclosure. For example, such an antibody may have the same $V_H$ and/or $V_L$ CDRs as clone SHB-617 as determined by the Chothia numbering scheme. In another example, an anti-PD-1 antibody within the scope of the present disclosure may have the same $V_H$ and/or $V_L$ CDRs as clone SHB-617 as determined by the Kabat numbering scheme.

Alternatively, the anti-PD-1 antibody described herein may comprise a $V_H$ chain at least 75% (e.g., 80%, 85%, 90%, 95%, or 98%) identical to the $V_H$ chain (mature or precursor) of SHB-617 and/or a $V_L$ chain at least 75% (e.g., 80%, 85%, 90%, 95%, or 98%) identical to the $V_L$ chain (mature of precursor) of SHB-617.

The "percent identity" of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In other examples, the anti-PD-1 antibody described herein may comprise a $V_H$ chain that includes up to 5 (e.g., 1, 2, 3, 4, or 5) amino acid residue variations in the $V_H$ CDR regions ($V_H$ CDR1, CDR2, and/or CDR3) as compared to the $V_H$ CDRs of SHB-617, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_L$ CDRs of SHB-617.

The anti-PD-1 antibody as described herein may be a chimeric antibody derived from SHB-617. Such a chimeric antibody can include a $V_H$ and $V_L$ chains derived from SHB-617 (as those described herein) and a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In other examples, the anti-PD-1 antibody described herein is a humanized antibody derived from SHB-617. A "humanized antibody" can be an antibody derived from modifying a non-human antibody to replace certain antibody fragments (e.g., framework regions) with those from a human antibody so as to reduce immunogenicity in humans. The humanized antibody described herein can be in any antibody form. In some embodiments, they are intact immunoglobulin molecules (full-length antibodies), including IgG, IgA, IgD, IgE, and IgM. In other embodiments, the humanized antibodies are antigen binding fragments thereof, e.g., Fab, F(ab')$_2$, scFv and Fv. In some instances, they also can be single-chain antibodies or bi-specific antibodies.

Humanized antibodies can be designed as follows. First, the variable regions of $V_H$ and $V_L$ of a parent non-human antibody are subjected to three-dimensional molecular modeling analysis following methods known in the art. See, e.g., Queen et al., *Proc. Natl. Acad. Sci. USA*, 86:10029-10033 (1989). Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

Examples of the chimeric and humanized anti-PD-1 antibodies derived from SHB-617 described herein are provided below (see also FIGS. 2-5; and Examples 1-3):
SHB-617 Sequences (Rat/Human IgG4/Kappa Chimera)

```
Heavy chain full length amino acid sequence
(448 AA; SEQ ID NO: 19)
QVTLKESGPGILQPSQTLSLTCSFSGFSLSTSGTCVSWIRQPSGKGLEW
LATICWEDSKGYNPSLKNRLTISKDTSNNQAFLKITSVDTADSAIYYCA
RREDSGYFWFPYWGQGTLVSVSSASTKGPSVFPLAPCSRSTSESTAALG
CLVKDYFPEPVTVSWNSGALTSGVHTFPAVLQSSGLYSLSSVVTVPSSS
LGTKTYTCNVDHKPSNTKVDKRVESKYGPPCPPCPAPEFLGGPSVFLFP
PKPKDTLMISRTPEVTCVVVDVSQEDPEVQFNWYVDGVEVHNAKTKPRE
EQFNSTYRVVSVLTVLHQDWLNGKEYKCKVSNKGLPSSIEKTISKAKGQ
PREPQVYTLPPSQEEMTKNQVSLTCLVKGFYPSDIAVEWESNGQPENNY
KTTPPVLDSDGSFELYSRLTVDKSRWQEGNVESCSVMHEALHNHYTQKS
LSLSLGK Heavy chain full length coding sequence
                                  (SEQ ID NO: 20)
CAGGTGACACTCAAGGAAAGCGGACCTGGAATCCTCCAACCTTCCCAGA
CTCTTTCCCTGACCTGTAGCTTCTCCGGGTTCTCCTTGTCCACCTCTGG
CACATGCGTGTCATGGATCAGACAGCCATCTGGGAAGGGCTTGGAGTGG
CTGGCAACAATTTGCTGGGAGGATTCAAAGGGGTACAACCCAGTCTGA
AGAACAGGCTGACCATTAGCAAGGACACCAGCAACAATCAGGCCTTCCT
GAAAATTACTAGCGTCGATACAGCTGACAGCGCCATCTACTACTGCGCC
CGCCGGGAGGACAGCGGGTACTTTTGGTTTCCCTATTGGGGCCAGGGCA
CTCTCGTCTCCGTGAGCAGTgctagcactaaggggccatcagtgttccc
cctggcccatgcagccggagtacaagcgaatccactgccgcccttgga
tgcctcgtgaaggattacttccccgagcccgtgaccgtgagttggaaca
gcggagccttgacaagcggcgtccacacattcccgccgtcctccagtc
tagcgggctttacagcctcagctccgtcgtgaccgtccctagttcctcc
ctcggaactaagacatacacttgcaacgtggatcataagccctcaaaca
caaaggtcgataagcgggtcgagagcaaatacggccaccatgcccacc
ttgtcccgccccgagttttggggggccctctgtgttcctctttcct
cctaagcctaaggacactctcatgattagccggacaccgaggtcacct
gcgtcgtcgtggacgtgagccaggaggaccctgaagtgcagttcaattg
gtatgtggacggggtcgaggtccacaacgccaagacaaagccaagagag
gagcagtttaacagtacctaccgggtcgtgagtgtgctgacagtgcttc
accaggactggctgaacgggaaggagtataagtgcaaggtgtccaacaa
gggcctcccctcaagcatcgagaagactatctctaaggccaaggggcag
cccagagagccacaggtgtatacattgcccctagccaggaggagatga
ctaaaaccaggtgtctctgacctgtctggtcaaaggcttctacccctc
cgatatcgctgtggagtgggagtccaacggacagccagaaaacaactac
aagaccacacctcccgtcctggatagcgacggctcatttttcctataca
gcaggctgaccgtggacaaatccagatggcaggagggcaacgtgttctc
```

```
ctgcagcgtgatgcatgaggccctgcacaaccactacactcagaagtcc ctgtccctgagcctgggcaaatag

Light chain full length amino acid sequence
(213 AA; SEQ ID NO: 21)
NIQMTQSPSLLSASVGDRVTLSCKAGQNVNNYLAWYQQKLGEPPKVLIF

NANSLQTGVPSRFSGSGSGTDFTLTISSLQPEDVATYFCQQYNSWTTFG

AGTKLELKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

Light chain full length coding sequence
(SEQ ID NO: 22):
AATATCCAGATGACCCAGTCCCCTTCCCTCCTCAGCGCTTCCGTGGGAG

ATAGGGTGACACTCAGTTGCAAGGCAGGACAGAACGTGAACAACTACCT

GGCCTGGTACCAGCAGAAGCTGGGCGAACCTCCAAAGGTCCTTATCTTC

AACGCCAACAGCCTGCAGACCGGGGTGCCCTCACGGTTTTCTGGGTCTG

GGAGCGGCACAGACTTTACTTTGACTATTAGCTCCTTGCAGCCCGAGGA

CGTCGCCACATATTTCTGTCAGCAATACAACAGCTGGACCACCTTCGGG

GCCGGCACAAAGCTGGAGCTGAAAcgtacggtggctgcaccatctgtct tcatcttcccgccatctgatgagcagttgaaatctggaactgcctctgt tgtgtgcctgctgaataacttctatcccagagaggccaaagtacagtgg aaggtggataacgccctccaatcgggtaactcccaggagagtgtcacag agcaggacagcaaggacagcacctacagcctcagcagcaccctgacgct gagcaaagcagactacgagaaacacaaagtctacgcctgcgaagtcacc catcagggcctgagctcgcccgtcacaaagagcttcaacaggggagagt gttag
```

Humanized SHB-617 (SSI-361) Variable Regions

```
>SSI-361_VL amino acid sequence
                                     (SEQ ID NO: 11)
NIQMTQSPSSLSASVGDRVTITCKAGQNVNNYLAWYQQKPGKAPKVLIF

NANSLQTGVPSRFSGSGSGTDFTLTISSLQPEDFATYYCQQYNSWTTFG

GGTKVEIKR

>SSI-361_VH amino acid sequence
                                     (SEQ ID NO: 12)
QVTLKESGPALVKPTQTLTLTCTFSGFSLSTSGTCVSWIRQPPGKALEW

LATICWEDSKGYNPSLKSRLTISKDTSKNQAVLTMTNMDPVDTATYYCA

RREDSGYFWFPYWGQGTLVTVSS
```

Humanized SHB-617 in Human IgG4S228P/Kappa (SSI-361)

```
Heavy chain full length sequence
(448 AA; SEQ ID NO: 23))
QVTLKESGPALVKPTQTLTLTCTFSGFSLSTSGTCVSWIRQPPGKALEW

LATICWEDSKGYNPSLKSRLTISKDTSKNQAVLTMTNMDPVDTATYYCA

RREDSGYFWFPYWGQGTLVTVSSASTKGPSVFPLAPCSRSTSESTAALG

CLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLGK

Light chain full length sequence
(213 AA; SEQ ID NO: 24)
NIQMTQSPSSLSASVGDRVTITCKAGQNVNNYLAWYQQKPGKAPKVLIF

NANSLQTGVPSRFSGSGSGTDFTLTISSLQPEDFATYYCQQYNSWTTFG

GGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC
```

Also described herein are functional variants of the above disclosed exemplary humanized anti-PD-1 antibody SSI-361. Such functional variants can comprise a $V_H$ chain that comprises an amino acid sequence at least 85% (e.g., 90%, 92%, 94%, 95%, 96%, 97%, 98%, or 99%) identical to that of SSI 361 and/or a $V_L$ chain that has an amino acid sequence at least 85% (e.g., 90%, 92%, 94%, 95%, 96%, 97%, 98%, or 99%) identical to that of SSI 361. These variants are capable of binding to an PD-1 molecule, particularly a human PD-1 antigen. In some examples, the variants possess similar antigen-binding affinity relative to the exemplary humanized antibody described above (e.g., having a $Kd<100\times10^{-9}M$).

In some embodiments, the functional variants described above contain one or more mutations (e.g., conservative substitutions) in the FRs of either the $V_H$ or the $V_L$ as compared to those in SSI-361. Preferably, such mutations do not occur at residues which are predicted to interact with one or more of the CDRs (see Example 2 below). As known in the art, mutations within the FR regions are unlikely to affect the antigen-binding activity of the antibody. In other embodiments, the functional variants described herein contain one or more mutations (e.g., 1, 2, or 3) within one or more of the CDR regions. Preferably, such functional variants retain the same regions/residues responsible for antigen-binding as the parent, such as the same specificity-determining residues inside the CDRs.

Any of the anti-PD-1 antibodies can be prepared via conventional methodology, e.g., recombination technology. See, e.g., Green et al. (1994) Nature Genetics 7, 13; and U.S. Pat. Nos. 5,545,806 and 5,569,825.

When a full-length antibody is desired, coding sequences of any of the anti-PD-1 antibody $V_H$ and $V_L$ chains described herein can be linked to the coding sequences of the Fc region of a human immunoglobulin and the resultant gene encoding a full-length antibody heavy and light chains can be expressed and assembled in a suitable host cell, e.g., a plant cell, a mammalian cell, a yeast cell, or an insect cell.

Antigen-binding fragments can be prepared via routine methods. For example, F(ab')2 fragments can be produced by pepsin digestion of an full-length antibody molecule, and Fab fragments that can be generated by reducing the disulfide bridges of F(ab')2 fragments. Alternatively, such fragments can be prepared via recombinant technology by expressing the heavy and light chain fragments in suitable host cells (e.g., E. coli, yeast, mammalian, plant, or insect cells) and have them assembled to form the desired antigen-binding fragments either in vivo or in vitro.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

A humanized anti-PD-1 antibody produced as described above can be examined to determine their properties, such as antigen-binding activity and biological function, following routine methods, e.g., those described in Example 3 below.

Also disclosed herein are nucleic acids encoding any of the anti-PD-1 antibodies described herein, vectors such as expression vectors or recombinant viruses comprising these nucleic acids, and host cells comprising the vectors. In one example, both the heavy and light chain coding sequences are included in one expression vector. Each of the heavy chain coding sequence and the light chain coding sequence may be in operable linkage to a suitable promoter. Alternatively, expression of both the heavy chain and the light chain may be driven by the same promoter. In another example, each of the heavy and light chains of the antibody is cloned in to an individual vector. In the latter case, the expression vectors encoding the heavy and light chains can be co-transfected into one host cell for expression of both chains, which can be assembled to form intact antibodies either in vivo or in vitro. Alternatively, the expression vector encoding the heavy chain and that encoding the light chain can be introduced into different host cells for expression each of the heavy and light chains, which can then be purified and assembled to form intact antibodies in vitro. Suitable host cells include, but are not limited to, mammalian cells (e.g., CHO cells or 293 cells), plant cells, insect cells, yeast cells, or bacterial cells. Recombinant viruses such as oncolytic viruses capable of expressing SSI-361 or its fragments may be used to for therapeutic applications.

The present disclosure also provides an immunoconjugate comprising any of the anti-PD-1 antibodies described herein and a suitable agent, which can be a therapeutic agent or diagnostic agent. In some examples, the anti-PD-1 antibody disclosed herein is linked to a cytotoxic agent, a radioisotope, or a drug. Methods for preparing such an immunoconjugate are well known in the art. See, e.g., WO 2014/160160, U.S. Pat. Nos. 5,208,020 and 5,416,064; and Chari et al., 1992 Cancer Res. 52:127-131. For example, the antibody may be modified with a bifunctional agent such as N-Succinimidyl-3-(2-pyridyldithio) propionate (SPDP) to introduce an active disulfide moiety. If needed, the agent to be conjugated to the antibody may be modified to introduce a thiol-group following routine practice. Reaction with the thiol-containing agent would produce an immunoconjugate in which the antibody and the agent are linked via disulfide bonds.

Uses of Anti-PD-1 Antibodies

The anti-PD-1 antibodies described herein (either in free form or as an immunoconjugates) can be used as therapeutic agents and diagnostic agents, as well as research tools in biochemistry, molecular biology, and medical researches.

Accordingly, disclosed herein are methods for treating a disease associated with the PD-1 signaling (e.g., cancer such as lung, colon, stomach, liver, bladder, or breast cancers etc.) comprising administering to a subject in need of the treatment an effective amount of any of the anti-PD-1 antibodies described herein. Such antibodies can also be used to enhance immune responses such as T cell activation in a subject in need of the treatment. In one example, a subject (e.g., a human patient) who needs the just-noted treatment is a patient having, suspected of having, or at risk for cancer development. In some embodiments, any of the anti-PD-1 antibodies described herein can be used for treating PD-L1 positive tumors. For example, a human patient suitable for the treatment can be identified by examining whether such a patient carries PD-L1 positive cancer cells. A human patient who would be suitable for the treatment described herein can be a cancer patient carrying PD-L1 positive cancer cells.

As used herein, the term "treating" refers to the application or administration of a composition including one or more active agents to a subject, who has a disorder/disease associated with the signaling pathway mediated by PD-1 (e.g., those described herein), a symptom of the disease/disorder, or a predisposition toward the disease/disorder, with the purpose to cure, heal, alleviate, relieve, alter, remedy, ameliorate, improve, or affect the disease/disorder, the symptom of the disease/disorder, or the predisposition toward the disease/disorder.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, the amount of the anti-PD-1 antibody described herein is effective in suppressing the PD-1 signaling (e.g., reducing the PD-1 signaling by at least 20%, 30%, 50%, 80%, 100%, 200%, 400%, or 500% as compared to a blank control). In other embodiments, the amount of the anti-PD-1 antibody described herein is effective in activating immune responses (e.g., by at least 20%, 30%, 50%, 80%, 100%, 200%, 400%, or 500% as compared to a blank control).

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to the desired therapeutic effects. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

To practice a treatment disclosed herein, any of the anti-PD-1 antibody or the encoding nucleic acid can be mixed with a pharmaceutically acceptable carrier to form a pharmaceutical composition for administration to a subject in need of the treatment. A pharmaceutically acceptable carrier is compatible with the active ingredient(s) in the composition (and preferably, capable of stabilizing it) and not deleterious to the subject to be treated. For example, solubilizing agents such as cyclodextrins, which form more soluble complexes with a anti-PD-1 antibody as described herein, or a nucleic acid encoding such, or more solubilizing agents, can be utilized as pharmaceutical carriers for delivery of the agonist/antagonist. Examples of other carriers include colloidal silicon dioxide, magnesium stearate, sodium lauryl sulfate, and D&C Yellow #10. See, e.g., Remington's Pharmaceutical Sciences, Edition 16, Mack Publishing Co., Easton, Pa. (1980); and Goodman and Gilman's "The Pharmacological Basis of Therapeutics", Tenth Edition, Gilman, J. Hardman and L. Limbird, eds., McGraw-Hill Press, 155-173, 2001.

The pharmaceutical compositions, formulated for therapeutic uses, may be prepared for storage by mixing an agent having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

To treating a target disease, an effective amount of the pharmaceutical composition noted above can be administered to a subject (e.g., a human) in need of the treatment via a suitable route. A human subject who needs the treatment may be a human patient having, at risk for, or suspected of having a disorder associated with the signaling pathway mediated by PD-1. Such a patient can be identified by routine medical examination.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

If necessary, the pharmaceutical composition described herein, containing an anti-PD-1 antibody or its encoding nucleic acid(s), can be co-administered with a second therapeutic agent. The selection of the second therapeutic agent depends on the type of the disease to be treated. For example, if the target disease is cancer, the second agent can be an anti-cancer agent (e.g., Tamoxifen, Taxol, Erlotinib, Dexasone, and Herceptin).

When the pharmaceutical composition described here is co-used with a second therapeutic agent, a sub-therapeutic dosage of either the composition or of the second agent, or a sub-therapeutic dosage of both, can be used in the treatment of a subject having, or at risk of developing a disease or disorder associated with the cell signaling mediated by PD-1. Target diseases include cancer (e.g., those described herein), infectious diseases such as diseases caused by viral, bacterial, or fungus infection, or other diseases associated with immune deficiency, such as T cell dysfunction. Diseases caused by viral infection include, but are not limited to, HAV, HBV, and HCV.

A "sub-therapeutic dose" as used herein refers to a dosage, which is less than that dosage which would produce a therapeutic result in the subject if administered in the absence of the other agent or agents. Thus, the sub-therapeutic dose of an agent is one which would not produce the desired therapeutic result in the subject in the absence of the administration of the agents of the invention. Therapeutic doses of many agents that are in clinical use are well known in the field of medicine, and additional therapeutic doses can be determined by those of skill without undue experimentation. Therapeutic dosages have been extensively described in references such as Remington's Pharmaceutical Sciences, 22th ed., 2012; as well as many other medical references relied upon by the medical profession as guidance for the treatment of diseases and disorders.

Conventional methods, known to those of ordinary skill in the art of medicine, can be used to administer the pharmaceutical composition to the subject, depending upon the type of diseases to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

When a nucleic acid(s) encoding an anti-PD-1 antibody as described herein is used as the therapeutic agent, the nucleic acid(s) or a vector(s) expressing the antibody can be delivered to a subject by methods, such as that described in Akhtar et al., 1992, Trends Cell Bio. 2, 139. For example, it can be introduced into cells using liposomes, hydrogels, cyclodextrins, biodegradable nanocapsules, or bioadhesive microspheres. Alternatively, the nucleic acid or vector can be locally delivered by direct injection or by use of an infusion pump. Other approaches include employing various transport and carrier systems, for example through the use of conjugates and biodegradable polymers.

To facilitate delivery, any of the anti-PD-1 antibody or its encoding nucleic acids can be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle). The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the oligonucleotide/interfering RNA is encapsulated. Methods for preparing such a micelle, liposome, nanoparticle, or microsphere are well known in the art. See, e.g., U.S. Pat. Nos. 5,108,921; 5,354,844; 5,416,016; and 5,527,5285.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the antisense oligonucleotide into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with the antisense oligonucleotide, causing it to condense (e.g., reduce the size of the oligonucleotide), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

Combined Therapy

Also provided herein are combined therapies for any of the diseases associated with the PD-1 signaling as described herein with any of the anti-PD-1 antibodies described herein and a suitable second agent. The term combination therapy, as used herein, embraces administration of these agents (e.g., an anti-PD-1 antibody such as those described herein and a second suitable therapeutic agent) in a sequential manner, that is, wherein each therapeutic agent is administered at a different time, as well as administration of these therapeutic agents, or at least two of the agents, in a substantially simultaneous manner. Sequential or substantially simultaneous administration of each agent can be affected by any appropriate route including, but not limited to, oral routes, intravenous routes, intramuscular, subcutaneous routes, and direct absorption through mucous membrane tissues. The agents can be administered by the same route or by different routes. For example, a first agent (e.g., an anti-PD-1 antibody) can be administered orally, and a second agent (e.g., an anti-cancer agent, an anti-infection agent; or an immune modulator) can be administered intravenously. Further, an agent of the combination selected may be administered by intravenous injection while the other agents of the combination may be administered orally. Alternatively, for example, two or more of the agents may be administered by intravenous or subcutaneous injection.

As used herein, the term "sequential" means, unless otherwise specified, characterized by a regular sequence or order, e.g., if a dosage regimen includes the administration of an anti-PD-1 antibody and the second agent, a sequential dosage regimen could include administration of the anti-PD-1 antibody before, simultaneously, substantially simultaneously, or after administration of the second agent, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two compounds separately). As used herein, concurrent administration and substantially simultaneous administration are used interchangeably. Sequential administration refers to temporally separated administration of the agents described herein.

Combination therapy can also embrace the administration of the agents described herein in further combination with other biologically active ingredients. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks. When the target disease is cancer, the anti-PD-1 antibody may also be used before or after a surgery or radiotherapy.

It should be appreciated that any combination as described herein may be used in any sequence for treating the target disease described herein. The combinations described herein may be selected on the basis of a number of factors, which include but are not limited to the effectiveness of inhibiting or preventing the target disease progression, the effectiveness for mitigating the side effects of another agent of the combination, or the effectiveness of mitigating symptoms related to the target disease. For example, a combined therapy described herein may reduce any of the side effects associated with each individual members of the combination.

Examples of suitable agents for co-use with any of the anti-PD-1 antibodies include an antibody binding to a co-stimulatory receptor (e.g., CD137/4-1BB, OX40, CD40, ICOS, CD27, HVEM or GITR), an agent that induces immunogenic cell death (e.g., a chemotherapeutic agent, a radiotherapeutic agent, an anti-angiogenic agent, or an agent for targeted therapies), an agent that inhibits a checkpoint molecule (e.g., CTLA4, LAG3, TIM3, B7H3, B7H4, BTLA, or TIGIT), a cancer vaccine, an agent that modifies an immunosuppressive enzyme (e.g., IDO1 or iNOS), an agent that targets $T_{reg}$ cells, an agent for adoptive cell therapy, or an agent that modulates myeloid cells.

Kits for Use in Enhancing Immune Responses and Treating Diseases Associated with PD-1 Signaling The present disclosure also provides kits for use in enhancing immune responses and/or treating diseases associated with the PD-1 signaling. Such kits can include one or more containers comprising an anti-PD-1 antibody as described herein. In some embodiments, the kit can comprise instructions for use in accordance with any of the methods described herein. The included instructions can comprise a description of administration of the anti-PD-1 antibody to enhance immune responses and/or to treating a target disease as described herein. The kit may further comprise a description of selecting an individual suitable for treatment based on identifying whether that individual has a disease associated with the PD-1 signaling, e.g., those described herein.

The instructions relating to the use of an anti-PD-1 antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating any of the target diseases disclosed herein or alleviating one or more symptoms of such a disease may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-PD-1 antibody as described herein.

The kits described herein may include one or more additional therapeutic agents such as those described in the "Combination Treatment" above.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press;

Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Generation of Lead Anti-PD-1 Antibodies

Reagents and Methods

Human PD-1 protein (cat#1086-PD, Fc chimera), PD-L1 (cat#156-B7, Fc chimera), and antigen affinity-purified polyclonal goat IgG against human PD-1 (cat#AF1086) were purchased from R&D Systems (USA). Monoclonal mouse anti-human PD-1 IgG (clone J116, cat#16-9989-82) was purchased from eBiosciences (USA). Stable CHO cell line expressing human PD-1 was developed by transfection with full length human PD-1 cDNA (Gene ID: 5133).

Capture ELISA to detect anti-PD-1 antibodies was carried out by coating plates with streptavidin followed by biotin-PD-1. Antibody samples bound to PD-1 were detected by secondary antibodies (goat anti-mouse or rat IgG) conjugated with peroxidase.

FACS to detect anti-PD-1 antibodies was performed with CHO-PD-1 cell line. After incubating with antibody samples, CHO-PD-1 cells were detected by PE or FITC labeled secondary antibodies by FACS.

Blockade of PD-1 and PD-L1 binding was measured by FACS with CHO-PD-1 cells. PD-L1 was incubated with CHO-PD-1 cells followed by competition with anti-PD-1 antibody samples. The bound PD-L1 was then detected with anti-human Fc secondary antibody conjugated with Alexa 488.

Hybridoma Development and Lead Antibody Identification

Balb/c mice and Wistar rats were immunized with recombinant human PD-1 protein (R&D, cat#1086-PD, Fc chimera). The anti-PD-1 serum titers of the immunized animals were monitored by capture ELISA with biotin-PD-1 and human Fc as counter screen. The positive titers were further confirmed with FACS with CHO-PD-1 cells. One mouse and one rat with the highest titers were sacrificed, and spleenocytes were isolated and fused with SP2/0 myeloma cells using standard hybridoma protocol.

Twenty 96-well plates of mouse hybridomas were screened by capture ELISA with biotin-PD-1 and identified 334 positive wells. The positive samples were then tested by human Fc counter screen and 85 clones were identified as PD-1 specific. Next, these specific clones were tested for binding to CHO-PD-1 by FACS and top 34 clones were identified for further screening to block PD-L1 binding to CHO-PD-1 by FACS.

Further, twenty-five 96-well plates of rat hybridomas were screened by capture ELISA with biotin-PD-1 and identified 207 positive wells. The positive samples were then tested by human Fc counter screen and 54 clones were identified as PD-1 specific. Next, these specific clones were tested for binding to CHO-PD-1 by FACS and identified top 30 clones for further screening to block PD-L1 binding to CHO-PD-1 by FACS.

A PD-1/PD-L1 blockade assay was used to screen positive hybridoma samples. 24 clones with specific binding to PD-1 and ability to block PD-L1 binding to cellular PD-1 were identified. The top 13 hybridomas (5 rat and 8 mice) were cloned, produced and purified antibodies from 8 single cell clones including 1 rat IgM and 7 mouse IgG hybridomas. These purified antibodies were confirmed to bind human PD-1 protein and cellular PD-1, and block PD-L1 binding to cellular PD-1.

The antibody variable domains of these confirmed hybridomas were sequenced as follows. Briefly, total RNA was extracted from frozen hybridoma cells and cDNA was synthesized from the RNA using isotype-specific anti-sense primers or universal primers following the technical manual of SuperScript III First-Strand Synthesis System. The antibody fragments of $V_H$ and $V_L$ were amplified according to the standard operating procedure of RACE of GenScript. Amplified antibody fragments were separately cloned into a standard cloning vector using standard molecular cloning procedures. Colony PCR screening was performed to identify clones with inserts of correct sizes. Five single colonies with correct $V_H$ and $V_L$ insert sizes were sent for sequencing. The $V_H$ and $V_L$ genes of five different clones were found nearly identical. The consensus sequence is believed to be the sequence of the antibody produced by the hybridoma.

The cDNA sequences encoding the anti-PD-1 antibody variable domain sequences were synthesized as chimeras to human IgG4 heavy chain constant regions containing the hinge S228P (EU numbering; Kabat numbering 241) stabilizing mutation (Angal et., Mol. Immunol 30:105, 1993) or human kappa light chain constant region. HEK293 transient expression was carried out with plasmids containing the corresponding heavy and light chain sequences. These chimeric antibodies were purified by protein A affinity chromatography. The purified antibodies were buffered exchanged to PBS and checked for endotoxin (<5 EU/mg) and monomer (>95%).

Figure 1:
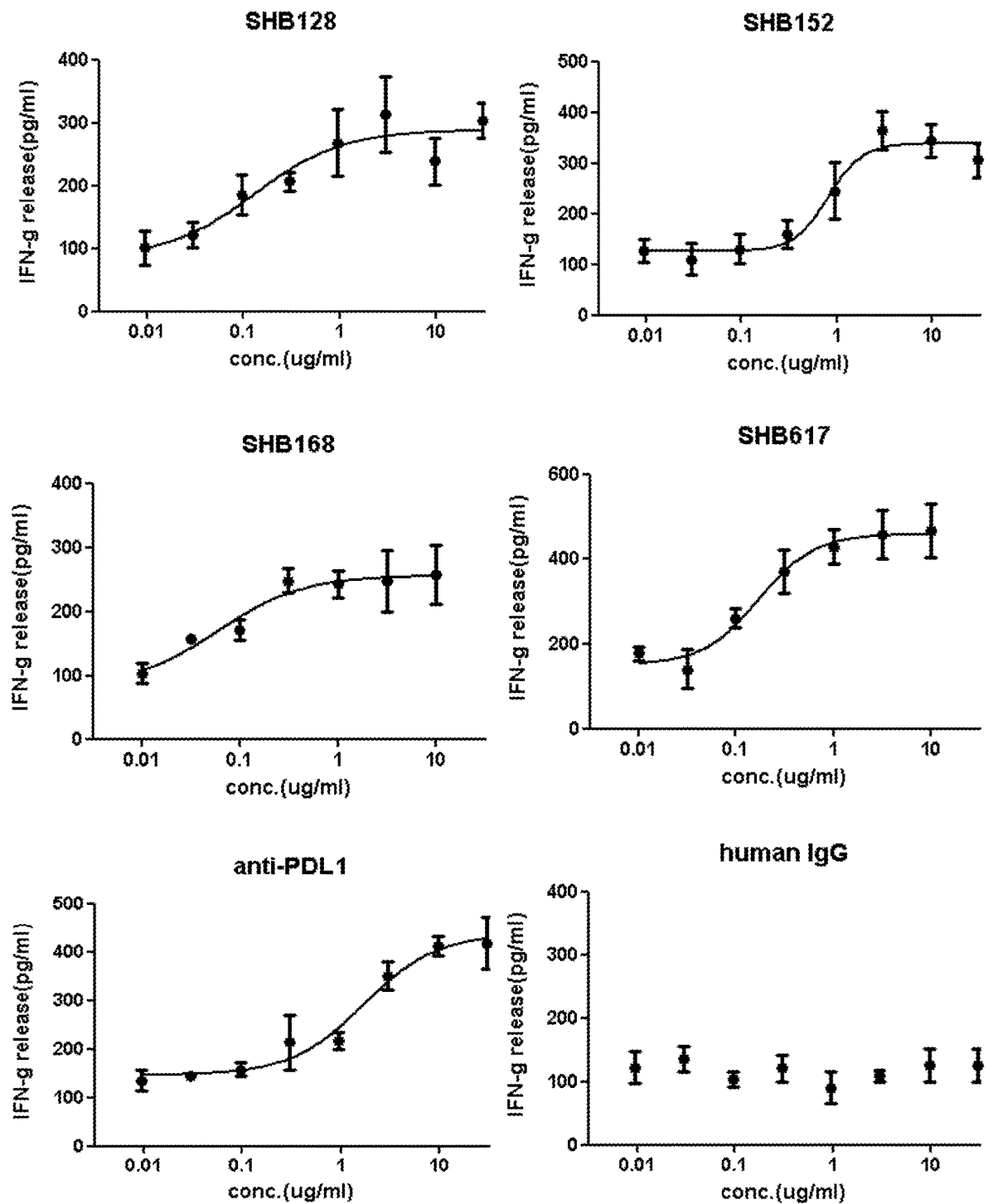
FIG. 1 is a series of graphs showing the comparison of anti-PD-1 chimeric antibodies in stimulating memory T cell response including: SHB-128, SHB-152, SHB-168 and SHB-617 chimeric antibodies, against human PD-1. Anti-PD-L1 and human IgG are used as positive and negative controls.

The chimeric antibodies were tested in functional assays for their activity to stimulate human T cell function in vitro. Fresh PBMC were isolated from volunteers who were recently immunized with tetanus toxoid vaccines. The cells were re-suspended in PRMI-1640 containing 10% FBS at 1*10^6/ml and plated into 96-well plate, 200 ul/well. The testing antibodies were diluted in PBS-BSA and added to the PMBC culture at final concentrations of 0, 0.03, 0.1, 0.3, 1, 3, 10 and 30 ug/ml. After 30 minutes of incubation, tetanus toxoid antigen (Astarte Biologics, cat#1002) was added to the PBMC culture. The plate was returned into incubator at 37° C. and 5% CO2 for 7 days. The IFN-γ in the culture supernatants were determined by ELISA (eBioscience, 88-7316-88). A positive control antibody against human PD-L1 (eBioscience #16-5983) was used. The SHB-617 (rat/human IgG4/kappa) chimera showed the highest maximal induction of IFNγ secretion from the activated T cells (FIG. 1). SHB-617 was derived from rat IgM. The activity of SHB-617 indicated that its binding domains possess unique activity in blocking PD-1 function.

Example 2: Humanization of the Lead Anti-PD-1 Antibody

SHB-617 was humanized as described herein and the humanized antibody thus obtained were further characterized. The amino acid sequences of the lead antibody SHB-617 were analyzed and annotated with the updated Chothia CDR definitions (Al-Lazikani et al, 1997). The CDR regions (L1, L2, L3, H1, H2 and H3) in the variable domains are shown in FIG. 2 and FIG. 3. Positional numbering is ordinal unless otherwise specified, in which case Chothia 1987 numbering will be used.

Sequence alignments comparing SHB-617 variable domains to human germlines were generated. Based on overall sequence identity, matching interface positions and similarly classed CDR canonical positions, a germline family was identified for each of the light and heavy chains as containing the most appropriate Acceptor frameworks, VK1-L1 for the light chain and VH2-2-70 for the heavy chain. The J-segment genes were compared to the Parental sequence over FR4 and the J-segments JK4 and JH4 were selected for the light and heavy chain respectively. Alignments of the Parental sequences to the Acceptor framework are shown in FIG. 2 and FIG. 3.

Humanization of SHB-617 was performed by via CDR-grafting to the selected human frameworks. Structural models of the Parental and the humanized sequences were constructed. Of note are the two cysteine residues present in FR2 (Cys35) and CDR H2 (Cys54). Cysteine residues are found at these positions in some murine germline sequences and it is possible that these residues can form a disulfide bond, which would potentially stabilize the VH domain. Additional intra heavy chain disulfide bonds were created within each model between the residues H:Cys35 and H:Cys54 for modeling purposes. H:Cys35 in FR2 was retained in the humanized sequence. In addition, germlining substitution of H:Asn67 in FR3 to threonine is not suitable due to the conformation of this position. Thus a substitution to serine is made as it is more compatible with the local conformation. No back mutation of the light chain frame work was made. Alignments of the variable domains of the humanized and parental light and heavy chains are shown in FIGS. 4 and 5.

Recombinant full human IgG4/kappa of humanized SHB-617 was constructed with human IgG4 containing the hinge S228P (EU numbering; Kabat numbering 241) stabilizing mutation (Angal et., Mol. Immunol 30:105, 1993) and human kappa light chain constant region. The humanized SSI-361 antibody was expressed in and purified from HEK293 cells or CHO cells.

Example 3. Evaluation of Anti-PD-1 Chimeric Antibodies

KD Measurement of PD-1 Antigen Binding on Biacore

Flow cells of a Series S CM5 sensor chip (GE Healthcare Life Sciences) were activated with freshly mixed 50 mmol/L NHS and 200 mmol/L EDC for 360 seconds (10 μL/min). Then, anti-His IgGs, in 10 mmol/L NaAC (pH 5.0) was injected onto the activated flow cell (10 μL/min) for 300 seconds (10 μL/min) with HBS-EP+(10 mM HEPES, 150 mM NaCl, 3 mM EDTA and 0.05% P20, pH 7.4) as the running buffer. The remaining active coupling sites were blocked with a 420 second injection of 1 mol/L ethanolamine (10 μL/min). This procedure was repeated for 2 times to immobilized protein on 2 flow cells individually. Low flow rate overnight was maintained for the equilibrium of the immobilized proteins. Human PD-1 was captured on a flow cell 2 (10 μL/min). Serially diluted SSI-361 (3.125 nM, 6.25 nM, 12.5 nM, 25 nM and 50 nM) was injected onto the antigen captured flow cell at 30 ul/min for 180 seconds and dissociated for 600 seconds, with duplicated injection for one concentration of antigen. Flow cell 1 without captured antigen was used as reference flow cell. To remove the tested antibody and antigen from the surface, 10 mM glycine-HCl pH 1.5 was injected for 60s (10 μL/min, flow cell 1-2). The above procedures were repeated for each concentration of serially diluted tested antibody. The KD value (Table 1) was evaluated using Biacore X100 evaluation software 2.0 with 1:1 interaction binding model. Flow cell 1 was used as reference flow cell for data subtraction.

TABLE 1

Binding kinetics of SSI-361 by Biacore analysis

| Antigen | ka (1/Ms) | kd (1/s) | KD (M) |
| --- | --- | --- | --- |
| Human PD-1 | 2.296E+5 | 1.165E−3 | 5.072E−9 | ka: association constant; kd: dissociation constant; KD: affinity constant.

PD-1 Binding ELISA

Figure 6:
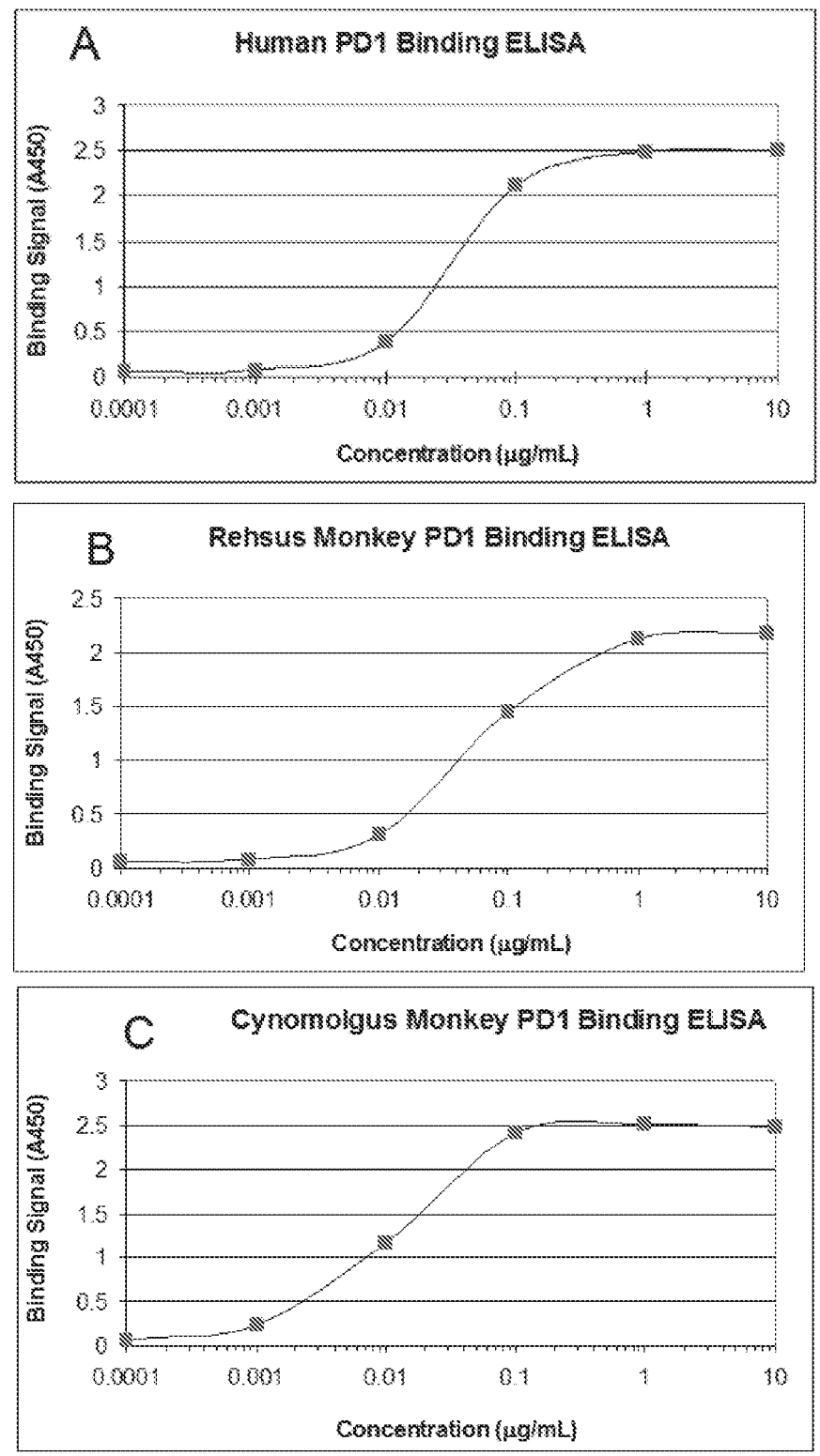
FIG. 6 includes graphs that show binding to human and monkey PD-1 protein by ELISA. Panel A: Human PD-1 binding ELISA. Panel B: Rehsus monkey PD-1 binding ELISA. Pane C: Cynomolgus monkey PD-1 binding ELISA.

The PD-1 antibody sample was diluted in PBS to 1 ug/ml and was coated in an ELISA plate (Costar, Cat#3590, high binding) 100 ul/well, 4° C. overnight. The plate was decanted and blocking solution (eBioscience, ELISA/ELISPOT Diluent, Cat#00-4202-55) was added 200 ul/well. After 1 hour incubation at room temperature, the plate was washed with PBST three times. Human PD-1-His tag protein (Sino Biological Inc. Cat#10377-H08H-100), or rhesus monkey PD-1-His (Sino Biological Inc. Cat#90305-KO8H-100), was diluted in blocking buffer to 0, 0.001, 0.01, 0.1, 1.10 ug/ml and added to the plate 100 ul/well. The plate was incubated 1 hour at room temperature and then washed four times with PBST. Anti-His-HRP (Genscript Cat#A00612) at 1:2000 dilution was added to the plate 100 ul/well. The plate was incubated 1 hour at room temperature followed by washing with PBST four times. The TMB substrate solution was added 100 ul/well. Let the color develop for 15 minutes and add 50 ul/well 1M H2SO4 to terminate the reaction. Absorbance at 450 nm was determined in FlexStation 3 ELISA reader. Graphpad 5.0, "log(agonist) vs. response—Variable slope" was used to calculate ELISA binding EC50 value (0.33 nM and 0.39 nM for human and rhesus monkey PD-1, respectively) (FIG. 6, Panels A & B).

To determine binding to PD-1 of cynomolgus monkey, Cyno PD-1—Fc tag (Sino Biological Inc. Cat#90311-CO2H) was diluted in PBS to 2 ug/ml, and 100 ul/well was used to coat an ELISA plate (Costar, Cat#3590, high binding), 4° C. overnight. The plate was decanted and blocking solution (eBioscience, ELISA/ELISPOT Diluent, Cat#00-4202-55) was added, 200 ul/well. After 1 hour incubation at room temperature, the plate was washed with PBST three times. The testing PD-1 antibody was diluted in blocking buffer to 0, 0.001, 0.01, 0.1, 1.10 ug/ml and added to the plate, 100 ul/well. The plate was incubated 1 hour at room temperature and then washed four times with PBST. Anti-Hu IgG-HRP (goat-anti-human Ig kappa-HRP, Millipore, Cat# AP502P) at 1:4000 dilution was added to the plate, 100 ul/well. The plate was incubated 1 hour at room temperature followed by washing with PBST four times. The TMB substrate solution was added 100 ul/well. The color developed for 15 minutes and 50 ul/well of 1M H2SO4 was added to terminate the reaction. Absorbance at 450 nm was determined in FlexStation 3 ELISA reader. Graphpad 5.0, "log (agonist) vs. response—Variable slope" was used to calculate ELISA binding EC50 value (0.08 nM) (FIG. 6, Panel C).

PD-1 Binding FACS

Figure 7:
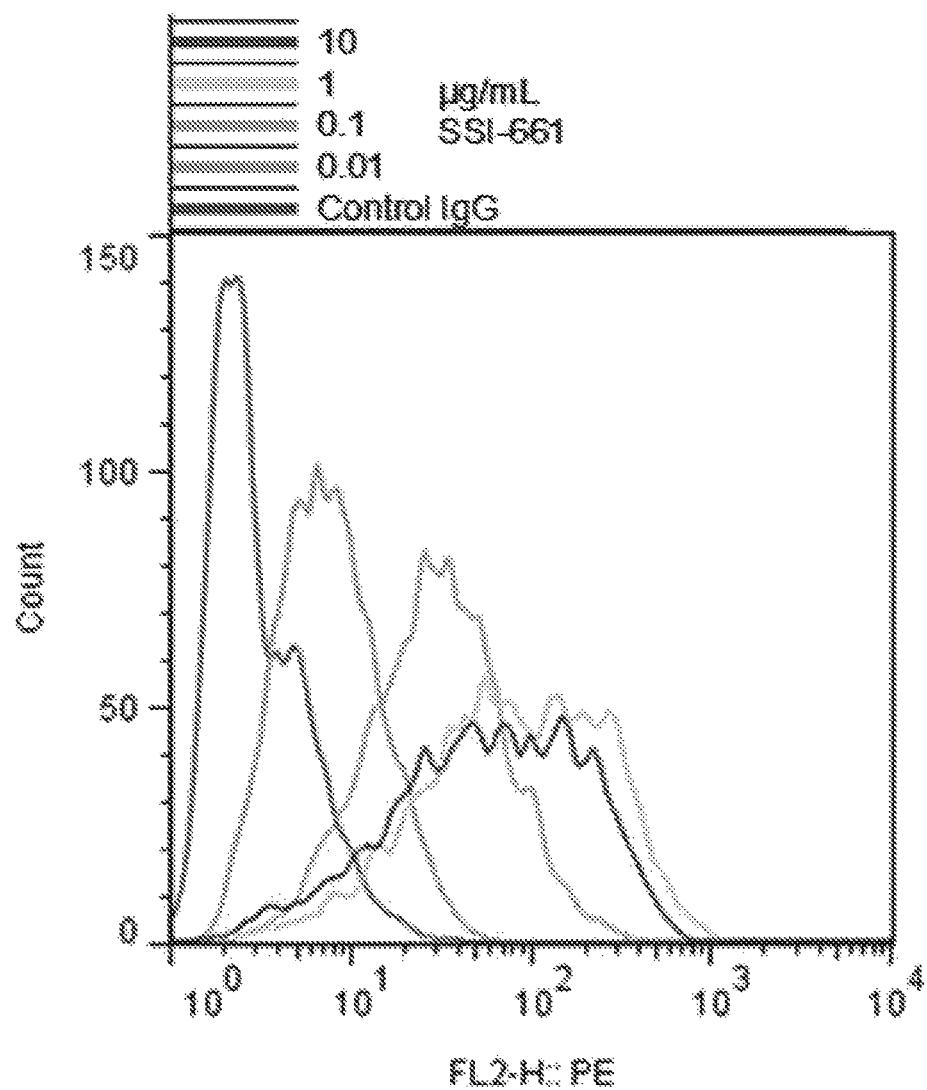
FIG. 7 is a graph showing binding to cellular human PD-1 by FACS.

CHO cells over-expressing human PD-1 were harvested by centrifugation at 1000 rpm for 5 minutes. The cells were resuspended in cold PBS-BSA at 5*10^6/ml and aliquoted 100 ul/vial. PD-1 antibody was diluted in PBS-BSA at 3×(final concentrations at 0, 0.01, 0.1, 1 and 10 ug/ml) and 50 ul was added to the CHO-PD-1 cells. The cell solutions were mixed and incubated 4° C. in dark for 1 hour. The cells were washed with PBS-BSA two times. Secondary antibody conjugates (PE Mouse Anti-Human IgG in staining buffer. BD, Cat#555787) 100 ul/vial was added and cells were mixed and incubated 4° C. in dark for 1 hour. The cells were then washed twice with PBS-BSA followed by fixation and FACS analysis with FACScaliber. As shown in FIG. 7, SSI-361 at 1 µg/mL (~6.7 nM) concentration saturated human PD-1 on the CHO cells over-expressing human PD-1.

PD-L1/2 Blockade

Figure 8:
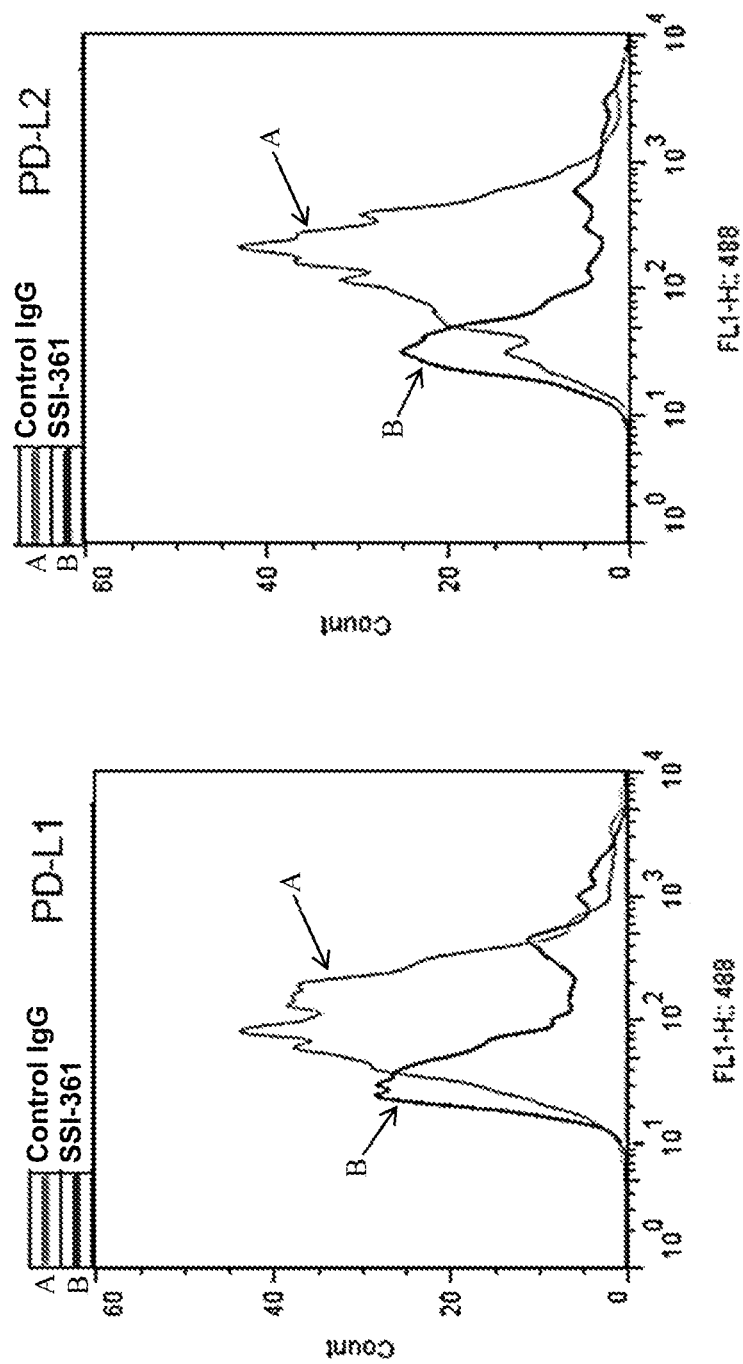
FIG. 8 shows two graphs depicting the blockade of human ligand binding to cellular human PD-1.

CHO cells over-expressing human PD-1 were harvested by centrifugation at 1000 rpm for 5 minutes. The cells were resuspended in cold PBS-BSA at 5*10^6/ml and aliquoted 100 ul/vial. PD-1 antibody was diluted in PBS-BSA at 4×(final concentration 1 ug/ml) and 50 ul was added to the CHO-PD-1 cells. 50 ul 4× human PD-L1 (Sino Biological Inc. Cat#10084-H08H-100) was added at final 2 ug/ml or 50 ul 4× human PD-L2 (Sino Biological Inc. Cat#10292-H08H-100) at final 1 ug/ml. The cell solutions were mixed and incubated 4° C. in dark for 4 hours. The cells were washed with PBS-BSA two times. 100 ul 2 ug/ml anti-His Tag Antibody [iFluor 488] (GenScript, Cat# A01800-100) was added and cells were mixed and incubated 4° C. in dark for 1 hour. The cells were then washed twice with PBS-BSA followed by fixation and FACS analysis with FACScaliber. SSI-361 at 1 ug/ml effectively blocked the binding of human PD-1 with PD-L1 and PD-L2 (FIG. 8).

T Cell Functional Assays

Figure 9:
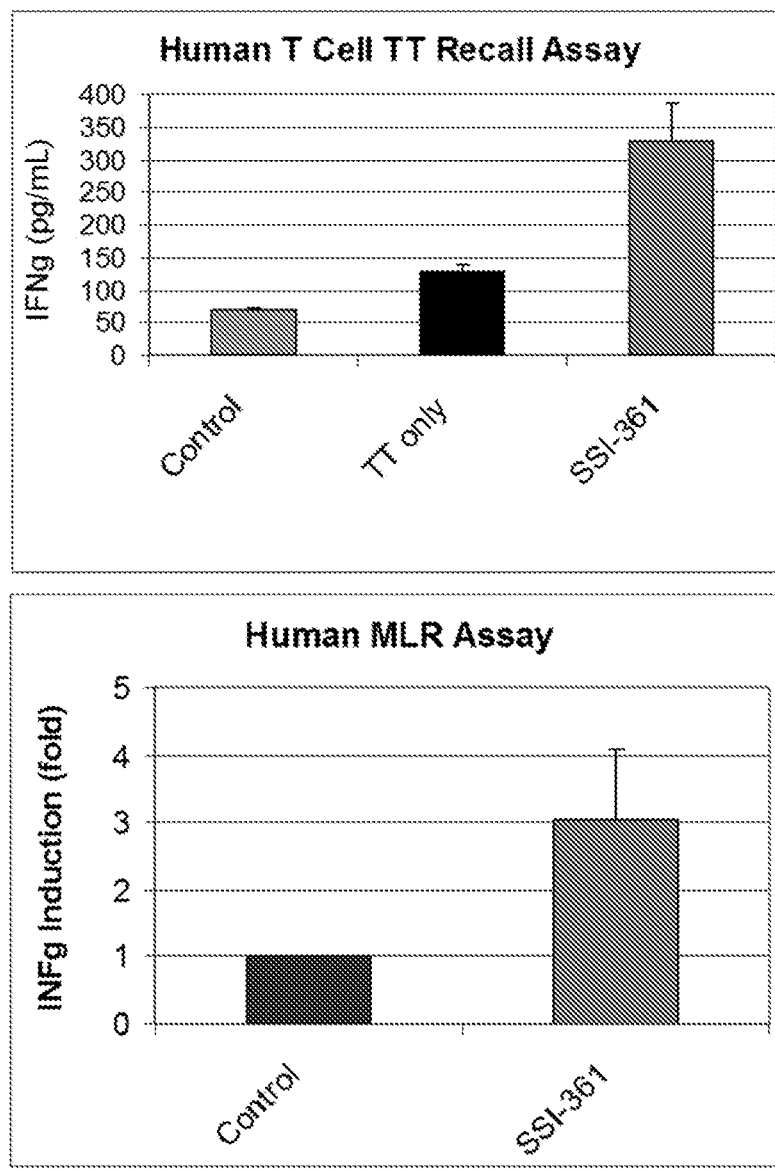
FIG. 9 shows two bar graphs depicting the stimulation of human T cell activation.

Fresh PBMC was isolated from volunteers who were recently immunized with tetanus toxoid vaccines. The cells were resuspended in PRMI-1640 containing 10% FBS at 1*10^6/ml and plated into 96-well plate, 200 ul/well. The testing antibodies were diluted in PBS-BSA and added to the PMBC culture at final concentration of 3 ug/ml. After 30 minutes incubation, tetanus toxoid antigen (Astarte Biologics, cat#1002) was added to the PBMC culture at a final concentration of 1 ug/ml. The plate was returned into incubator at 37° C. and 5% CO2 for 7 days. The IFN-g in the culture supernatants were determined by ELISA (eBioscience, 88-7316-88). SSI-361 at 3 ug/ml enhanced tetanus toxoid antigen induced IFN-g secretion (FIG. 9).

Mixed lymphocyte reaction (MLR) was used to examine the activity of SSI-361. Fresh PBMC was isolated from volunteers and the cells were resuspended in PRMI-1640 serum-free at 2*10^6/ml and plated into 6-well plate, 200 ul/well. After incubation at 37° C., 5% CO2 for 1.5 hours, unattached cells were removed and 2 ml RPMI-1640 medium containing 50 ng/ml GM-CSF and 35 ng/ml IL-4 (Peprotech, AF-HDC). The plate was returned to incubator for 7 days and fresh medium was replaced every 2 days. On day 7, LPS was added to the culture at 1 ug/ml to induce dendritic cell maturation for another day. Mitomycin (Sigma, M0503-2MG) at 10 ug/ml was added to the culture for 1.5 hour, and the dendritic cells were harvested and washed with RPMI medium for use in MLR assay described below.

EasySep™ Human T Cell Isolation Kit (Stemcell, Cat#17951) was used to isolate human T cells. PBMC was diluted in EasySep™ buffer at 5*10^7/ml, and Isolation Cocktail antibodies were added as instructed. After mixing and sitting at room temperature for 5 minutes, RapidSpheres magnetic beads were added, followed by addition of 5 ml EasySep™ buffer. The T cells were harvested after removal of non-T cells with the EasySep™ magnets.

The allergenic dendritic cells and T cells were resuspended in RPMI-1640 medium at density of 1*10^6/ml and 1*10^5/ml, respectively. 100 ul of each cell types were added into the wells of 96-well culture plate. PD-1 antibodies were added to the culture mix at final concentration of 3 ug/ml. The plate was returned to incubator at 37° C., 5% CO2 for 5 days. The IFN-g in the culture supernatants were determined by ELISA (eBioscience, 88-7316-88). SSI-361 increased IFG-g secretion from the MLR (FIG. 9).

Pharmacokinetics in Cynomolgus Monkey

Figure 10:
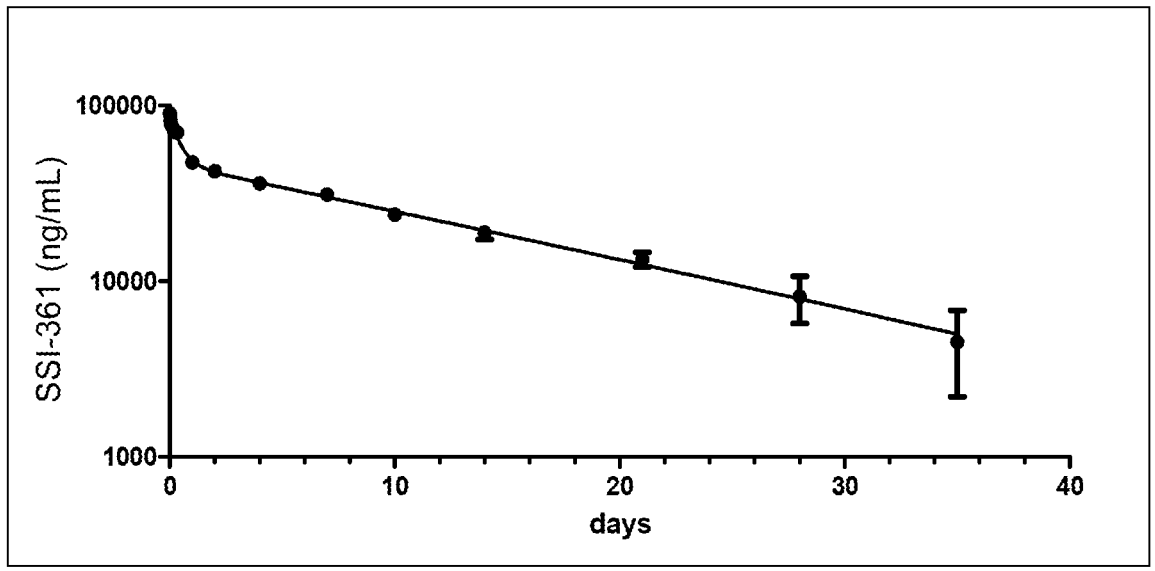
FIG. 10 is a graph showings pharmacokinetics of SSI-361 in cynomolgus monkeys.

The pharmacokinetic (PK) profile of SSI-361 following single intravenous injection in cynomolgus monkeys was determined. Four female cynomolgus monkeys of weight around 3 kg were used. PD-1 antibody SSI-361 was prepared in PBS and dosed at 5 mg/kg by intravenous injections. Serum samples were harvested at 0, 5, 30 min, 1, 2, 4, 8 hr, 1, 3, 5, 8, 11, 15, 22, 29 and 36 day time points by venipuncture of peripheral veins. The serum samples were stored at −80° C. before ELISA assays were performed to determine SSI-361 concentrations. Human PD-1 (Sino Biological Inc. Cat#10377-H08H-100)) was diluted in PBS to 2 ug/ml, and 100 ul/well was used to coat an ELISA plate (Costar, Cat#3590, high binding), 4° C. overnight. The plate was decanted and blocking solution (eBioscience, ELISA/ELISPOT Diluent, Cat#00-4202-55) was added 200 ul/well. After 1 hour incubation at room temperature, the plate was washed with PBST three times. The testing samples with proper dilutions in blocking were added to the plate, 100 ul/well. The plate was incubated 1 hour at room temperature and then washed four times with PBST. Anti-Hu IgG-HRP (goat-anti-human Ig kappa-HRP, Millipore, Cat# AP502P) at 1:4000 dilution was added to the plate 100, ul/well. The plate was incubated 1 hour at room temperature followed by washing with PBST four times. The TMB substrate solution was added, 100 ul/well. The color developed for 15 minutes and added 50 ul/well of 1M H2SO4 to terminate the reaction. Absorbance at 450 nm was determined in FlexStation 3 ELISA reader. SSI-661 concentrations in the samples were calculated from standard curve and shown in FIG. 10. PK parameters were calculated and listed as in Table 2.

TABLE 2

Pharmacokinetic parameters of SSI-361 following single IV dose in cynomolgus monkeys.

| Dose (mg/kg) | $t_{1/2}$ (day) | $AUC_{all}$ (mg*hr/mL) | $AUC_{Inf}$ (mg*hr/mL) | $V_{ss}$ (mL/kg) | CL (mL/hr/kg) |
|---|---|---|---|---|---|
| 3 | 13.4 | 16.3 | 18.5 | 60.0 | 0.167 |

Example 4: In Vivo Efficacy of Anti-PD-1 Antibodies Against Tumor in Syngenic Mouse Model The objective of this study was to verify the in vivo efficacies of SSI-361 (PD-1 Ab01) along with commercially purchased antibody Opdivo (nivolumab) PD-1 Ab02 in the treatment of tumors induced by MC38-huPD-L1 cells (colon adenocarcinoma cells transfected with human PD-L1) in human PD-1 knocked-in (hPD-1 KI) mice. An exemplary experimental design is provided in Table 3 below:

TABLE 3

Experimental Design

| Group | N | Treatment | Dose (mg/kg) | Dosing route | Planned Schedule |
|---|---|---|---|---|---|
| 1 | 8 | PBS | 0 | i.p. | BIW x3 wks |
| 2 | 8 | PD-1 Ab01 | 10 | i.p. | BIW x3 wks |
| 3 | 8 | PD-1 Ab02 | 10 | i.p. | BIW x3 wks |

The dosing volume is 10 μl/g.

24 male hPD-1 KI mice (background strain: C57BL/6), age 7.7 weeks (starting from the drug administration) were used in this study. The mice were kept in individually ventilated cage (IVC) systems at 20-24° C. and 30-70% humidity with 2 animals in each cage. The animals had free access to irradiation sterilized dry granule food and drinking water, which was sterilized by US and ozone, during the entire study period.

MC38-huPD-L1 cells were maintained in vitro as a suspension culture in RPMI-1640 Medium (without phenol red) with concentration of $1 \times 10^7$ cells/ml. Each mouse was inoculated subcutaneously into right side with $1 \times 10^6$ cells in 0.1 ml RPMI-1640 medium for tumor development. Tumor volumes of inoculated animals were checked twice weekly. At the 9th day after inoculation, the animals were randomly assigned into 3 different treatment groups. The average tumor volumes of these animals reached 68.3 mm³. Each group has 8 animals and two of them were kept in one cage. The anti-PD-1 antibodies were administered to the tumor-bearing mice according to the experimental design shown in Table 3. Administration of the anti-PD-1 antibodies began after randomization of the mice into the three study arms, which was denoted as day 0. Treatments were ended on day 17.

The animals were checked for any effects of tumor growth and treatments on normal behavior such as mobility, visual estimation of food and water consumption, body weight gain/loss (body weights were measured twice weekly or every other day), eye/hair matting and any other abnormal effect. Death and observed clinical signs were recorded on the basis of the numbers of animals within each subset. Twenty-four hours after the 4th dosing, 10 ul blood was collected through the tail nip to pre-labeled tubes with 40 ul PBS, mixed and stored at −80° C.

Tumor volumes were measured twice weekly in two dimensions using a caliper, and the volume was expressed in mm3 using the formula: TV=0.5a×b2 where a and b were the long and short diameters of the tumor, respectively. TV was further used for tumor growth inhibition (TGI) analysis following the formula: % TGI=(1−(Ti−T0)/(Ci−C0))×100%, in which Ti and Ci refer to mean tumor volume (MTV) of the treatment group and the control group on day I, and T0 and C0 refer to MTV of the treatment group and the control group on day 0. TV was also used for T-C analysis, following the formula: T−C=Tn−Cn, in which Tn refers to the time (days after treatment) when tumor volume reached n (e.g., 1000 mm³) in the treatment group (days); and Cn refers to the time (days after treatment) when tumor volume reached n (e.g., 1000 mm³) in the control group (days).

According to the experimental design, the study was terminated two weeks after the 6$^{th}$ dosing. The animals were euthanized individually or entirely when the following signs were observed: (a) when the animal was moribund, in severe distress or unable to obtain adequate food or water; (b) when body weight continued to drop and body weight loss was >20%; or (c) tumor volume of individual mice reached 3000 mm³ or MTV of entire group reached 1500 mm³.

The mean and the standard error of the mean (SEM) were calculated for the tumor volume and body weight of each group at each time point. Statistical analyses were carried out using Graph Pad Prism software. Significant differences in tumor growth were determined by Student's t test. Values of P<0.05 were considered significant.

Figure 11:
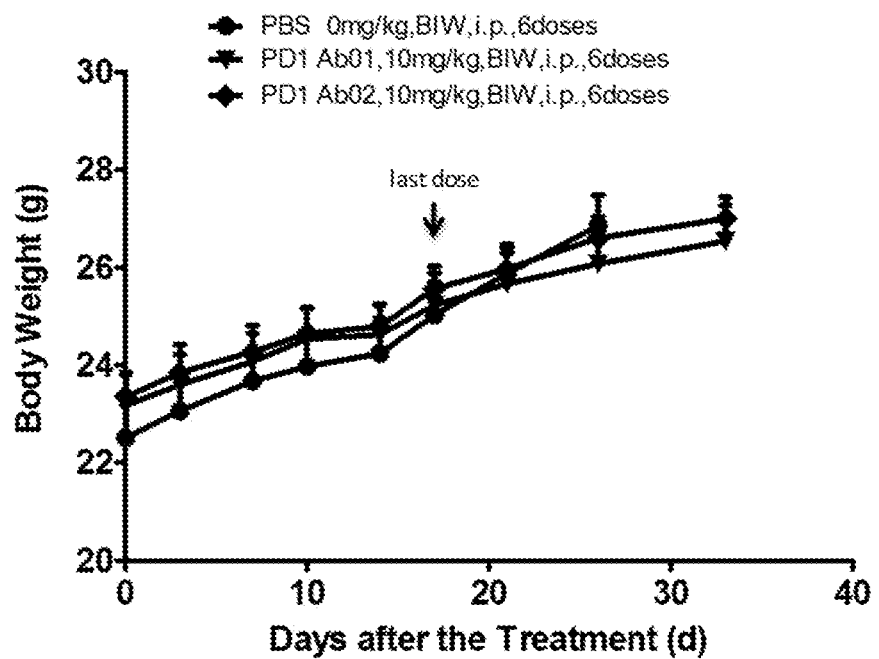
FIG. 11 is a chart showing body weight change of MC38-huPD-L1 bearing mice treated with anti-PD-1 antibodies or PBS as a vehicle control. When mean tumor volume reached 68.3 mm³, the mice were randomized into 3 study arms (n=8), each of which was treated with PBS, PD-1 Ab01 (SSI-361), or PD-1 Ab02 (nivolumab). Treatments were carried out twice weekly for 3 weeks. Error bars represented Mean±SEM. No significant influences on body weight were observed after PD-1 Ab01 and PD-1 Ab02 treatments.

The body weight change over the course of treatment is provided in FIG. 11. No significant influences on body weight were observed after PD-1 Ab01 and PD-1 Ab02 treatments. The tumor volumes and tumor growth inhibition of the different groups at different time points are shown in Table 4 and Table 5, respectively, below (Data represents "Mean±SEM"):

TABLE 4

Tumor Volumes

| | Tumor volume (mm³) | | |
|---|---|---|---|
| Days after Grouping | Group1 PBS | Group2 PD-1 Ab01 10 mg/kg | Group3 PD-1 Ab02 10 mg/kg |
| 0 | 68.4 ± 6.0 | 68.0 ± 5.7 | 68.5 ± 5.6 |
| 3 | 130.4 ± 17.5 | 91.2 ± 7.4 | 104.9 ± 8.3 |
| 7 | 245.0 ± 37.6 | 70.6 ± 7.8 | 127.5 ± 33.0 |
| 10 | 352.5 ± 69.0 | 38.7 ± 8.1 | 112.4 ± 49.3 |
| 14 | 486.0 ± 108.7 | 24.8 ± 11.5 | 129.6 ± 69.9 |
| 17 | 617.4 ± 161.7 | 24.3 ± 13.0 | 145.7 ± 82.9 |
| 21 | 1008.8 ± 303.8 | 28.1 ± 17.1 | 183.6 ± 101.7 |
| 26 | 1498.3 ± 455.4 | 34.5 ± 19.4 | 241.8 ± 135.8 |
| 33 | / | 62.9 ± 15.2 | 372.1 ± 197.8 |

TABLE 5

Tumor Growth Inhibition

| Groups | Treatment | TV of D0$^a$ (mm³) | TV of D21$^a$ (mm³) | TGI (%) | T-C (days) | P Value$^b$ |
|---|---|---|---|---|---|---|
| 1 | PBS | 68.4 ± 6.0 | 1008.8 ± 303.8 | — | — | — |
| 2 | PD-1 Ab01 (10 mg/kg) | 68.0 ± 5.7 | 28.1 ± 17.1 | 104.24 | — | <0.05 |
| 3 | PD-1 Ab02 (10 mg/kg) | 68.5 ± 5.6 | 183.6 ± 101.7 | 87.76 | — | <0.05 |

Figure 12:
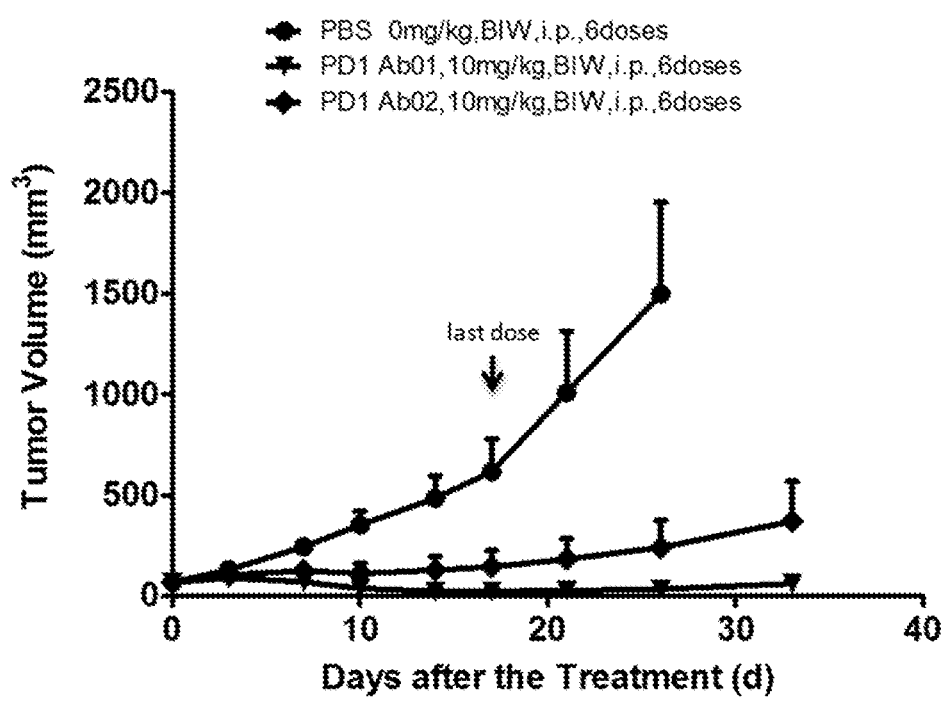
FIG. 12 is a chart showing the tumor volume change in MC38-huPD-L1 bearing mice treated with anti-PD-1 antibodies or PBS as a vehicle control. When mean tumor volume reached 68.3 mm³, the mice were randomized into 3 study arms (n=8), each of which was treated with PBS, PD-1 Ab01 (SSI-361), or PD-1 Ab02 (nivolumab). Treatments were carried out twice weekly for 3 weeks. Error bars represented Mean±SEM. PD-1 Ab01 and PD-1 Ab02 showed strong antitumor activities in hPD-1 KI mice transplanted with MC38-hPD-L1 tumor cells.

Further, as shown in FIG. 12, both anti-PD-1 antibodies showed significant tumor suppression activities in this study.

In summary, this study verified the therapeutic efficacies of two exemplary anti-PD-1 antibodies using the syngenic MC38-huPD-L1 tumor cell xenograft in hPD-1 KI mice. No significant body weight change was observed in the treated mice during the course of treatment.

The mean tumor volume in PBS-treated groups (BIW, 6 doses) reached 1008.8 mm$^3$, while both anti-PD-1 antibodies significantly reduced tumor volumes. The TGI (%) values for Ab01 and Ab02 were 104.24% and 87.76%, respectively. The tumor suppression levels of both antibodies were statistically significant as compared with the vehicle control group ($P<0.05$).

Example 5: Efficacy of Anti-PD-1 Antibodies in Treating Tumors Induced by MC38 and B16F1 Cancer Cells in Syngenic Mouse Model This study intends to evaluate the in vivo treatment efficacy of humanized anti-PD-1 antibodies using MC38 (PD-L1 positive) & B16F1 (PD-L1 negative) syngenic mouse model. An exemplary experimental design is provided in FIG. 13.

Transgenic mice having human PD-1 knocked-in (hPD-1 KI) were used in this study and C57BL/6 mice were used as controls. The hPD-1 KI mice were shown to be responsive to anti-human PD-1 antibody treatment in tumor xenograft models. FIG. 14. The hPD-1 KI mice and C57BL/6 mice were kept in individually ventilated cages at 20-24° C. and 30-70% humidity with 1-3 animals in each cage. The animals had free access to irradiation sterilized dry granule food and drinking water, which was sterilized by US and ozone, during the entire study period.

MC38 cells (colon adenocarcinoma cells) and B16F1 cells (skin melanoma cells) were cultured in RPMI 1640 in the presence of 10% FBS. The MC38 cells were maintained in vitro as a suspension culture at a concentration of $5 \times 10^6$ cells/ml.

PD-1Mice from Example 4 which were cured by the treatment of PD-1 antibodies as described, as well as control naïve mice, were then inoculated subcutaneously into right side with $5 \times 10^5$ cells in 0.1 ml RPMI-1640 medium for tumor development. Tumor volumes of inoculated animals were checked twice weekly. When the mean volume of the tumor induced by MC38 cells in the C57BL/6 mice reached 110.4 mm$^3$, B16F1 cells ($2 \times 10^5$ cells in 0.1 ml of RPMI-1640 medium) were inoculated subcutaneously into the left side of the same animal for tumor development. The animals were checked for any effects of tumor growth and treatments on normal behavior such as mobility, visual estimation of food and water consumption, body weight gain/loss (body weights were measured twice weekly or every other day), eye/hair matting and any other abnormal effect. Death and observed clinical signs were recorded on the basis of the numbers of animals within each subset.

Tumor volumes were measured twice weekly in two dimensions using a caliper, and the volume was expressed in mm3 using the formula: TV=0.5 a×b2 where a and b were the long and short diameters of the tumor, respectively.

According to the experimental design, B16F1 cells were inoculated into left side 9 days after MC38 cell inoculation. Tumor volumes of all animals were checked twice weekly for 24 days. The animals were then euthanized individually or entirely when the following signs were observed: (a) when the animal was moribund, in severe distress or unable to obtain adequate food or water; (b) When body weight continued to drop and body weight loss was >20%; or (c) MTV of entire group reached 1500 mm$^3$.

As shown in FIG. 15, no significant influences on body weight were observed in three study arms. The tumor volumes in anti-PD-1 antibody-treated mice were significantly lower than those in the control C57BL/6 mice, as shown in Table 6 below (tumor volume values refer to means±SEM):

Further, results obtained from this study show that there was no measureable growth in previously PD-1 Ab01 and PD-1 Ab02-treated mice; by contrast, tumors induced by MC38 cells showed normal growth curve in C57BL/6 mice. FIG. 16. The growth of B6F1 had no obvious differences in three study arms.

Overall, this study demonstrated that the anti-PD-1 antibodies successfully induced memory anti-tumor immunity that suppressed the growth of specific tumors in hPD-1 KI mice. The mice treated with anti-PD-1 antibody also showed no significant body weight change during the course of the experiments.

Table 6. Tumor Volumes

TABLE 6

Tumor Volumes
Tumor volume (mm$^3$)

| Days after inoculation | | Group1 PD-1 Ab01-treatment respond | | Group2 PD-1 Ab02-treatment respond | | Group3 C57BL/6 mice | |
|---|---|---|---|---|---|---|---|
| MC38 | B16F1 | MC38 | B16F1 | MC38 | B16F1 | MC38 | B16F1 |
| 0 | / | 0 ± 0 | / | 0 ± 0 | / | 0 ± 0 | / |
| 6 | / | 0 ± 0 | / | 0 ± 0 | / | 73.9 ± 4.0 | / |
| 8 | / | 0 ± 0 | / | 0 ± 0 | / | 95.1 ± 8.0 | / |
| 9 | 0 | 0 ± 0 | 0 ± 0 | 0 ± 0 | 0 ± 0 | 110.4 ± 9.0 | 0 ± 0 |
| 13 | 4 | 0 ± 0 | 0 ± 0 | 0 ± 0 | 0 ± 0 | 202.5 ± 21.9 | 0 ± 0 |
| 17 | 8 | 0 ± 0 | 0 ± 0 | 0 ± 0 | 4.8 ± 4.8 | 278.2 ± 31.5 | 0 ± 0 |
| 20 | 11 | 0 ± 0 | 9.6 ± 9.6 | 0 ± 0 | 28.5 ± 18.7 | 329.4 ± 57.3 | 9.0 ± 6.3 |
| 24 | 15 | 0 ± 0 | 91.7 ± 48.4 | 0 ± 0 | 115.1 ± 67.8 | 394.3 ± 105.7 | 51.0 ± 36.1 |
| 27 | 18 | 0 ± 0 | 204.0 ± 143.2 | 0 ± 0 | 328.1 ± 208.9 | 574.4 ± 183.0 | 184.2 ± 132.4 |
| 31 | 22 | 0 ± 0 | 915.3 ± 743.7 | 0 ± 0 | 853.0 ± 496.0 | 932.7 ± 283.1 | 751.0 ± 407.6 |
| 33 | 24 | 0 ± 0 | 1226.6 ± 940.4 | / | / | 1183.9 ± 330.0 | 1221.1 ± 558.2 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated anti-PD-1 antibody, which comprises:
   (i) a heavy chain variable region ($V_H$) that comprises a heavy chain complementary determining region (HC CDR) 1 set forth as GFSLSTSGT (SEQ ID NO:13), a HC CDR2 set forth as CWEDS(SEQ ID NO:14), and a HC CDR3 set forth as EDSGYFWFPY (SEQ ID NO:15); and
   (ii) a light chain variable region ($V_L$) that comprises a light chain complementary determining region (LC CDR) 1 set forth as KAGQNVNNYLA(SEQ ID NO:16), a LC CDR2 set forth as NANSLQT(SEQ ID NO:17); and a LC CDR3 set forth as QQYNSWTT (SEQ ID NO:18).

2. The isolated anti-PD-1 antibody of claim 1, wherein the antibody is a full-length antibody or an antigen-binding fragment thereof.

3. The isolated anti-PD-1 antibody of claim 2, wherein the full-length antibody is an IgG molecule.

4. The isolated anti-PD-1 antibody of claim 2, wherein the antigen-binding fragment is Fab or F(ab)'2 or scFv.

5. The isolated anti-PD-1 antibody of claim 1, wherein the antibody is a chimeric antibody or a humanized antibody.

6. The isolated anti-PD-1 antibody of claim 1, wherein the $V_H$ comprises an amino acid sequence at least 80% identical to QVTLKESGPALVKPTQTLTLTCTFSGFSLST-SGTCVSWIRQPPGKALEWLATICWEDSKGY NPSLKSRLTISKDTSKNQAVLTMTNMDPVDTATYY-CARREDSGYFWFPYWGQGTLVTV SS (SEQ ID NO:12).

7. The isolated anti-PD-1 antibody of claim 1, wherein the VL comprises an amino acid sequence at least 80% identical to NIQMTQSPSSLSASVGDRVTITCKAGQNVN-NYLAWYQQKPGKAPKVLIFNANSLQTGV PSRFSGSGSGTDFTLTISSLQPEDFATYYCQQYN-SWTTFGGGTKVEIKR (SEQ ID NO:11).

8. The isolated anti-PD-1 antibody of claim 1, wherein the $V_H$ comprises the amino acid sequence of QVTL-KESGPALVKPTQTLTLTCTFSGFSLST-SGTCVSWIRQPPGKALEWLATICWEDSKG YNPSLKSRLTISKDTSKNQAVLTMTNMDPVDTATYY-CARREDSGYFWFPYWGQGTLVT VSS (SEQ ID NO:12); and the $V_L$ comprises the amino acid sequence of NIQMTQSPSSLSASVGDRVTITCKAGQNVN-NYLAWYQQKPGKAPKVLIFNANSLQTGV PSRFSGSGSGTDFTLTISSLQPEDFATYYCQQYN-SWTTFGGGTKVEIKR (SEQ ID NO:11).

9. The isolated anti-PD-1 antibody of claim 8, wherein the $V_H$ consists of the amino acid sequence of QVTL-KESGPGILQPSQTLSLTCSFSGFSLST-SGTCVSWIRQPSGKGLEWLATICWEDSK GYNPSLKNRLTISKDTSNNQAFLKITSVDTADSAIYY-CARREDSGYFWFPYWGQGTLV SVSS (SEQ ID NO:12); and the $V_L$ consists of the amino acid sequence of NIQMTQSPSLLSASVGDRVTLSCKAGQNVN-NYLAWYQQKLGEPPKVLIFNANSLQTG VPSRFSGSGSGTDFTLTISSLQPEDVATYFCQQYN-SWTTFGAGTKLELKR (SEQ ID NO:11).

10. An isolated nucleic acid or a set of nucleic acids, which collectively encodes an anti-PD-1 antibody of claim 1.

11. The isolated nucleic acid or the set of nucleic acids of claim 10, which is a vector or a set of vectors.

12. The isolated nucleic acid or the set of nucleic acids of claim 11, wherein the vector(s) is an expression vector or a recombinant virus.

13. The isolated nucleic acid or the set of nucleic acids of claim 10, which is a single nucleic acid comprising a first nucleotide sequence that encodes the $V_H$ and a second nucleotide sequence that encodes the $V_L$.

14. The isolated nucleic acid or the set of nucleic acids of claim 10, which is a set of nucleic acids comprising a first nucleic acid that comprises a first nucleotide sequence encoding the $V_H$ and a second nucleic acid that comprises a second nucleotide sequence encoding $V_L$.

15. A vector or vector set comprising a nucleic acid or a set of nucleic acids of claim 10.

16. The vector or vector set of claim 15, which is expression vector(s).

17. A host cell comprising a vector or vector set of claim 15.

18. An immunoconjugate, comprising an anti-PD-1 antibody of claim 1 linked to a therapeutic or diagnostic agent.

19. A pharmaceutical composition, comprising an anti-PD-1 antibody of claim 1, or an immunoconjugate comprising the anti-PD-1 antibody linked to a therapeutic or diagnostic agent, and a pharmaceutically acceptable carrier.

20. A method for treating a cancer expressing PD-1 or PD-L1, the method comprising administering to a subject in need thereof an effective amount of the pharmaceutical composition of claim 19.

21. The method of claim 20, wherein the method further comprising administering the subject another therapeutic agent.

22. The method of claim 20, wherein the cancer expressing PD-1 or PD-L1 is colon cancer, lung cancer, stomach cancer, liver cancer, bladder cancer, breast cancer, or melanoma.

23. A method for preparing an anti-PD-1 antibody, the method comprising:
- (i) culturing a host cell that comprises a vector or vector set of claim 16 under conditions allowing for expression of the antibody; and
- (ii) collecting the host cell or the culture medium for isolation of the antibody.

\* \* \* \* \*

```
                         SEQUENCE LISTING

<160> NUMBER OF SEQ ID NOS: 24

<210> SEQ ID NO 1
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 1

Asn Ile Gln Met Thr Gln Ser Pro Ser Leu Leu Ser Ala Ser Val Gly
1               5                   10                  15

Asp Arg Val Thr Leu Ser Cys Lys Ala Gly Gln Asn Val Asn Asn Tyr
            20                  25                  30

Leu Ala Trp Tyr Gln Gln Lys Leu Gly Glu Pro Pro Lys Val Leu Ile
        35                  40                  45

Phe Asn Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Asn Ser Trp Thr Thr
                85                  90                  95

Phe Gly Ala Gly Thr Lys Leu Glu Leu Lys Arg
            100                 105

<210> SEQ ID NO 2
<211> LENGTH: 95
<212> TYPE: PRT
<213> ORGANISM: Artificial Sequence
<220> FEATURE:
<223> OTHER INFORMATION: Synthetic Polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 3
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 3

Leu Thr Phe Gly Gly Gly Thr Lys Val Glu Ile Lys
1               5                   10
```

<210> SEQ ID NO 4
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 4

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Thr Cys Val Ser Trp Ile Arg Gln Pro Ser Gly Lys Gly Leu Glu
        35                  40                  45

Trp Leu Ala Thr Ile Cys Trp Glu Asp Ser Lys Gly Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Ile Thr Ser Val Asp Thr Ala Asp Ser Ala Ile Tyr Tyr
                85                  90                  95

Cys Ala Arg Arg Glu Asp Ser Gly Tyr Phe Trp Phe Pro Tyr Trp Gly
            100                 105                 110

Gln Gly Thr Leu Val Ser Val Ser Ser
        115                 120
```

<210> SEQ ID NO 5
<211> LENGTH: 100
<212> TYPE: PRT
<213> ORGANISM: Artificial Sequence
<220> FEATURE:
<223> OTHER INFORMATION: Synthetic Polypeptide

<400> SEQUENCE: 5

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100
```

<210> SEQ ID NO 6
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 6

```
Tyr Phe Asp Tyr Trp Gly Gln Gly Thr Leu Val Thr Val Ser Ser
1               5                   10                  15
```

```
<210> SEQ ID NO 7
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 7

Asn Ile Gln Met Thr Gln Ser Pro Ser Ser Leu Ser Ala Ser Val Gly
1               5                   10                  15

Asp Arg Val Thr Ile Thr Cys Lys Ala Gly Gln Asn Val Asn Asn Tyr
            20                  25                  30

Leu Ala Trp Tyr Gln Gln Lys Pro Gly Lys Ala Pro Lys Val Leu Ile
        35                  40                  45

Phe Asn Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Trp Thr Thr
                85                  90                  95

Phe Gly Gly Gly Thr Lys Val Glu Ile Lys Arg
            100                 105

<210> SEQ ID NO 8
<211> LENGTH: 107
<212> TYPE: PRT
<213> ORGANISM: Rattus rattus

<400> SEQUENCE: 8

Asn Ile Gln Met Thr Gln Ser Pro Ser Leu Leu Ser Ala Ser Val Gly
1               5                   10                  15

Asp Arg Val Thr Leu Ser Cys Lys Ala Gly Gln Asn Val Asn Asn Tyr
            20                  25                  30

Leu Ala Trp Tyr Gln Gln Lys Leu Gly Glu Pro Pro Lys Val Leu Ile
        35                  40                  45

Phe Asn Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Asn Ser Trp Thr Thr
                85                  90                  95

Phe Gly Ala Gly Thr Lys Leu Glu Leu Lys Arg
            100                 105

<210> SEQ ID NO 9
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 9

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Thr Cys Val Ser Trp Ile Arg Gln Pro Pro Gly Lys Ala Leu Glu
        35                  40                  45

Trp Leu Ala Thr Ile Cys Trp Glu Asp Ser Lys Gly Tyr Asn Pro Ser
```

```
                50                  55                  60
Leu Lys Ser Arg Leu Thr Ile Ser Lys Asp Thr Ser Lys Asn Gln Ala
 65                  70                  75                  80

Val Leu Thr Met Thr Asn Met Asp Pro Val Asp Thr Ala Thr Tyr Tyr
                 85                  90                  95

Cys Ala Arg Arg Glu Asp Ser Gly Tyr Phe Trp Phe Pro Tyr Trp Gly
                100                 105                 110

Gln Gly Thr Leu Val Thr Val Ser Ser
            115                 120

<210> SEQ ID NO 10
<211> LENGTH: 121
<212> TYPE: PRT
<213> ORGANISM: Rattus rattus

<400> SEQUENCE: 10

Gln Val Thr Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Ser Thr Ser
                 20                  25                  30

Gly Thr Cys Val Ser Trp Ile Arg Gln Pro Ser Gly Lys Gly Leu Glu
             35                  40                  45

Trp Leu Ala Thr Ile Cys Trp Glu Asp Ser Lys Gly Tyr Asn Pro Ser
 50                  55                  60

Leu Lys Asn Arg Leu Thr Ile Ser Lys Asp Thr Ser Asn Asn Gln Ala
 65                  70                  75                  80

Phe Leu Lys Ile Thr Ser Val Asp Thr Ala Asp Ser Ala Ile Tyr Tyr
                 85                  90                  95

Cys Ala Arg Arg Glu Asp Ser Gly Tyr Phe Trp Phe Pro Tyr Trp Gly
                100                 105                 110

Gln Gly Thr Leu Val Ser Val Ser Ser
            115                 120

<210> SEQ ID NO 11
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 11

Asn Ile Gln Met Thr Gln Ser Pro Ser Ser Leu Ser Ala Ser Val Gly
  1               5                  10                  15

Asp Arg Val Thr Ile Thr Cys Lys Ala Gly Gln Asn Val Asn Asn Tyr
                 20                  25                  30

Leu Ala Trp Tyr Gln Gln Lys Pro Gly Lys Ala Pro Lys Val Leu Ile
             35                  40                  45

Phe Asn Ala Asn Ser Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Trp Thr Thr
                 85                  90                  95

Phe Gly Gly Gly Thr Lys Val Glu Ile Lys Arg
                100                 105

<210> SEQ ID NO 12
```

```
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 12

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Thr Cys Val Ser Trp Ile Arg Gln Pro Pro Gly Lys Ala Leu Glu
        35                  40                  45

Trp Leu Ala Thr Ile Cys Trp Glu Asp Ser Lys Gly Tyr Asn Pro Ser
    50                  55                  60

Leu Lys Ser Arg Leu Thr Ile Ser Lys Asp Thr Ser Lys Asn Gln Ala
65                  70                  75                  80

Val Leu Thr Met Thr Asn Met Asp Pro Val Asp Thr Ala Thr Tyr Tyr
                85                  90                  95

Cys Ala Arg Arg Glu Asp Ser Gly Tyr Phe Trp Phe Pro Tyr Trp Gly
            100                 105                 110

Gln Gly Thr Leu Val Thr Val Ser Ser
        115                 120

<210> SEQ ID NO 13
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 13

Gly Phe Ser Leu Ser Thr Ser Gly Thr
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 14

Cys Trp Glu Asp Ser
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 15

Glu Asp Ser Gly Tyr Phe Trp Phe Pro Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Polypeptide
```

<400> SEQUENCE: 16

Lys Ala Gly Gln Asn Val Asn Asn Tyr Leu Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 17

Asn Ala Asn Ser Leu Gln Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 18

Gln Gln Tyr Asn Ser Trp Thr Thr
1               5

<210> SEQ ID NO 19
<211> LENGTH: 448
<212> TYPE: PRT
<213> ORGANISM: Artificial Sequence
<220> FEATURE:
<223> OTHER INFORMATION: Synthetic Polypeptide

<400> SEQUENCE: 19

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Thr Cys Val Ser Trp Ile Arg Gln Pro Ser Gly Lys Gly Leu Glu
        35                  40                  45

Trp Leu Ala Thr Ile Cys Trp Glu Asp Ser Lys Gly Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Ile Thr Ser Val Asp Thr Ala Asp Ser Ala Ile Tyr Tyr
                85                  90                  95

Cys Ala Arg Arg Glu Asp Ser Gly Tyr Phe Trp Phe Pro Tyr Trp Gly
            100                 105                 110

Gln Gly Thr Leu Val Ser Val Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
      210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 20
<211> LENGTH: 1347
<212> TYPE: DNA
<213> ORGANISM: Artificial Sequence
<220> FEATURE:
<223> OTHER INFORMATION: Synthetic Polynucleotide

<400> SEQUENCE: 20
caggtgacac tcaaggaaag cggacctgga atcctccaac cttcccagac tctttccctg    60
acctgtagct tctccgggtt ctccttgtcc acctctggca catgcgtgtc atggatcaga   120
cagccatctg ggaagggctt ggagtggctg caacaatttg ctgggaggat tcaaaggggg   180
tacaacccca gtctgaagaa caggctgacc attagcaagg acaccagcaa caatcaggcc   240
ttcctgaaaa ttactagcgt cgatacagct gacagcgcca tctactactg cgcccgccgg   300
gaggacagcg ggtactttg gtttccctat tggggccagg gcactctcgt ctccgtgagc   360
agtgctagca ctaaggggcc atcagtgttc cccctggccc catgcagccg agtacaagc    420 gaatccactg ccgcccttgg atgcctcgtg aaggattact ccccgagcc cgtgaccgtg    480 agttggaaca gcggagcctt gacaagcggc gtccacacat tcccgccgt cctccagtct    540 agcgggcttt acagcctcag ctccgtcgtg accgtcccta gttcctccct cggaactaag    600
acatacactt gcaacgtgga tcataagccc tcaaacacaa aggtcgataa gcgggtcgag    660
agcaaatacg gcccaccatg cccaccttgt cccgcccccg agttttgggg gggcccctct    720

```
gtgttcctct ttcctcctaa gcctaaggac actctcatga ttagccggac acccgaggtc    780
acctgcgtcg tcgtggacgt gagccaggag gaccctgaag tgcagttcaa ttggtatgtg    840
gacggggtcg aggtccacaa cgccaagaca aagccaagag aggagcagtt taacagtacc    900
taccgggtcg tgagtgtgct gacagtgctt caccaggact ggctgaacgg gaaggagtat    960
aagtgcaagg tgtccaacaa gggcctcccc tcaagcatcg agaagactat ctctaaggcc   1020
aaggggcagc ccagagagcc acaggtgtat acattgcccc ctagccagga ggagatgact   1080
aaaaaccagg tgtctctgac ctgtctggtc aaaggcttct acccctccga tatcgctgtg   1140
gagtgggagt ccaacggaca gccagaaaac aactacaaga ccacacctcc cgtcctggat   1200
agcgacggct cattttcct atacagcagg ctgaccgtgg acaaatccag atggcaggag   1260
ggcaacgtgt tctcctgcag cgtgatgcat gaggccctgc acaaccacta cactcagaag   1320
tccctgtccc tgagcctggg caaatag                                        1347
```

<210> SEQ ID NO 21
<211> LENGTH: 213
<212> TYPE: PRT
<213> ORGANISM: Artificial Sequence
<220> FEATURE:
<223> OTHER INFORMATION: Synthetic Polypeptide

<400> SEQUENCE: 21

```
Asn Ile Gln Met Thr Gln Ser Pro Ser Leu Leu Ser Ala Ser Val Gly
1               5                   10                  15

Asp Arg Val Thr Leu Ser Cys Lys Ala Gly Gln Asn Val Asn Asn Tyr
            20                  25                  30

Leu Ala Trp Tyr Gln Gln Lys Leu Gly Glu Pro Pro Lys Val Leu Ile
        35                  40                  45

Phe Asn Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Asn Ser Trp Thr Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 22
<211> LENGTH: 642
<212> TYPE: DNA

<213> ORGANISM: Artificial Sequence
<220> FEATURE:
<223> OTHER INFORMATION: Synthetic Polynucleotide

<400> SEQUENCE: 22

```
aatatccaga tgacccagtc cccttccctc tcagcgctt  ccgtgggaga tagggtgaca      60
ctcagttgca aggcaggaca gaacgtgaac aactacctgg cctggtacca gcagaagctg     120
ggcgaacctc caaaggtcct tatcttcaac gccaacagcc tgcagaccgg ggtgccctca     180
cggttttctg gtctgggag cggcacagac tttactttga ctattagctc cttgcagccc     240
gaggacgtcg ccacatattt ctgtcagcaa tacaacagct ggaccacctt cggggccggc     300
acaaagctgg agctgaaacg tacggtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                        642
```

<210> SEQ ID NO 23
<211> LENGTH: 448
<212> TYPE: PRT
<213> ORGANISM: Artificial Sequence
<220> FEATURE:
<223> OTHER INFORMATION: Synthetic Polypeptide

<400> SEQUENCE: 23

```
Gln Val Thr Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Thr Cys Val Ser Trp Ile Arg Gln Pro Pro Gly Lys Ala Leu Glu
         35                  40                  45

Trp Leu Ala Thr Ile Cys Trp Glu Asp Ser Lys Gly Tyr Asn Pro Ser
     50                  55                  60

Leu Lys Ser Arg Leu Thr Ile Ser Lys Asp Thr Ser Lys Asn Gln Ala
 65                  70                  75                  80

Val Leu Thr Met Thr Asn Met Asp Pro Val Asp Thr Ala Thr Tyr Tyr
                 85                  90                  95

Cys Ala Arg Arg Glu Asp Ser Gly Tyr Phe Trp Phe Pro Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220
```

```
Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
    435                 440                 445
```

<210> SEQ ID NO 24
<211> LENGTH: 213
<212> TYPE: PRT
<213> ORGANISM: Artificial Sequence
<220> FEATURE:
<223> OTHER INFORMATION: Synthetic Polypeptide

<400> SEQUENCE: 24

```
Asn Ile Gln Met Thr Gln Ser Pro Ser Ser Leu Ser Ala Ser Val Gly
1               5                   10                  15

Asp Arg Val Thr Ile Thr Cys Lys Ala Gly Gln Asn Val Asn Asn Tyr
            20                  25                  30

Leu Ala Trp Tyr Gln Gln Lys Pro Gly Lys Ala Pro Lys Val Leu Ile
        35                  40                  45

Phe Asn Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Trp Thr Thr
            85                  90                  95

Phe Gly Gly Gly Thr Lys Val Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```